US009201008B2

(12) United States Patent
Thériault et al.

(10) Patent No.: US 9,201,008 B2
(45) Date of Patent: Dec. 1, 2015

(54) METHOD AND SYSTEM FOR OBTAINING AN EXTENDED-DEPTH-OF-FIELD VOLUMETRIC IMAGE USING LASER SCANNING IMAGING

(71) Applicant: UNIVERSITE LAVAL, Québec (CA)

(72) Inventors: Gabrielle Thériault, Québec (CA); Yves De Koninck, Québec (CA); Nathalie McCarthy, Québec (CA)

(73) Assignee: UNIVERSITE LAVAL, Québec (CA)

( * ) Notice: Subject to any disclaimer, the term of this patent is extended or adjusted under 35 U.S.C. 154(b) by 194 days.

(21) Appl. No.: 13/928,082

(22) Filed: Jun. 26, 2013

(65) Prior Publication Data

US 2014/0008549 A1   Jan. 9, 2014

Related U.S. Application Data

(60) Provisional application No. 61/664,452, filed on Jun. 26, 2012.

(51) Int. Cl.
*G01N 21/64* (2006.01)
*G02B 21/00* (2006.01)
*G02B 26/10* (2006.01)

(52) U.S. Cl.
CPC ............ *G01N 21/64* (2013.01); *G01N 21/6458* (2013.01); *G02B 21/002* (2013.01); *G02B 26/101* (2013.01); *G02B 26/105* (2013.01)

(58) Field of Classification Search
CPC   G01N 21/64; G01N 21/6428; G01N 21/6486
See application file for complete search history.

(56) References Cited

U.S. PATENT DOCUMENTS 3,013,467 A   12/1961   Minski
5,583,342 A   12/1996   Ichie
(Continued)

FOREIGN PATENT DOCUMENTS

EP             0627643 A2   12/1994
WO        2004075107 A2    9/2004
WO   WO 2011083420 A2 *   7/2011
OTHER PUBLICATIONS

Arimoto, Rieko et al. Imaging Properties of Axicon in a Scanning Optical System, Applied Optics, Nov. 1, 1992, 5 pages, vol. 31, No. 31.

(Continued)

*Primary Examiner* — Christine Sung
(74) *Attorney, Agent, or Firm* — Hovey Williams LLP

(57) ABSTRACT

A laser scanning imaging system and method for obtaining an extended-depth-of-field image of a volume of a sample are provided. The system includes a laser module generating an input laser beam, a beam shaping module including an axicon and a Fourier-transform lens, and an imaging module including an objective lens and a detecting assembly. The axicon, Fourier-transform lens and objective lens are formed and disposed to successively convert the input laser beam into an intermediate non-diffracting beam, an intermediate annular beam, and an excitation non-diffracting beam. The excitation beam is projected onto the sample and has a depth of field and transverse resolution together defining a three-dimensional excitation region. The detecting assembly collects electromagnetic radiation from the excitation region to obtain one pixel of the extended-depth-of-field image. The system further includes a two-dimensional scanning module for scanning the excitation beam over the sample and build, pixel-by-pixel, the extended-depth-of-field image.

20 Claims, 9 Drawing Sheets

(56) References Cited

U.S. PATENT DOCUMENTS

| | | | |
|---|---|---|---|
| 7,218,448 B1 | 5/2007 | Cathey, Jr. et al. | |
| 2002/0018197 A1* | 2/2002 | Suzuki | 355/403 |
| 2008/0089598 A1 | 4/2008 | George et al. | |
| 2008/0240347 A1 | 10/2008 | Bloom | |
| 2009/0091566 A1 | 4/2009 | Turney et al. | |
| 2009/0109417 A1* | 4/2009 | Tanitsu | 355/67 |
| 2009/0231650 A1* | 9/2009 | Minabe et al. | 359/11 |
| 2011/0205352 A1 | 8/2011 | Pavani et al. | |
| 2012/0057019 A1* | 3/2012 | Marchant | 348/135 |
| 2012/0212722 A1* | 8/2012 | Smith et al. | 355/67 |

OTHER PUBLICATIONS

Tucker, S. et al. Extended Depth of Field and Aberration Control for Inexpensive Digital Microscope Systems, Optics Express, May 24, 1999, p. 467-474, vol. 4., USA.

Konig, K, Multiphoton Microscopy in Life Sciences, Journal of Microscopy, Nov. 2000, p. 83-104, vol. 200.

Pologruto, T. et al. ScanImage: Flexible Software for Operating Laser Scanning Microscopes, BioMedical Engineering OnLin, May 7, 20013, p. 13, vol. 2, USA.

Burvall, A et al. Simple Lens Axicon, Applied Optics, 2004, p. 4838-4844, vol. 43.

Burvall, A., Axicon Imaging by Scalar Diffraction Theory, PhD Thesis, Royal Institute of Technology, 78 pages, Apr. 2004, Sweden.

Dufour, P. et al., Two-Photon Excitation Fluorescence Microscopy With a High Depth of Field Using an Axicon, Applied Optics, 2006, p. 9246-9252, vol. 45.

Botcherby, E.J et al., Scanning Two Photon Fluorescence Microscopy With Extended Depth of Field, Optics Communications, Jul. 14, 2006.

Gourley, K. et al. First Experimental Demonstration of a Fresnel Axicon, Spie Digital Library, 2008, 7 pages, vol. 7099.

Botcherby, E.J et al. Real-Time Extended Depth of Field Microscopy, Optics, Express, Dec. 22, 2008 p. 21843-21848, vol. 16.

Olivier, N. et al. Two-Photon Microscopy With Simultaneous Standard and Extended Depth of Field Using a Tunable Acoustic Gradient-Index Lens, Optic Letters, Jun. 1, 2009, vol. 34, No. 11.

Smith, C. et al. Extended Depth-of-Field Microscopy, Proceedings of SPIE, 2010, p. 75700s, vol. 7570.

Golub, I. et al. Characterization of a Refractive Logarithmic Axicon, Optic Letters, Aug. 15, 2010, p. 2828, vol. 35, No. 16.

Theriault, G. et al, Extended Depth of Field Microscopy for Rapid Volumetric Two-Photon Imaging, Optics Express, Apr. 2013, 10 pages, vol. 21. No. 08.

* cited by examiner

METHOD AND SYSTEM FOR OBTAINING AN EXTENDED-DEPTH-OF-FIELD VOLUMETRIC IMAGE USING LASER SCANNING IMAGING

RELATED PATENT APPLICATION

This application incorporates by reference, in its entirety, and claims priority to U.S. provisional patent application Ser. No. 61/664,452, filed Jun. 26, 2012.

FIELD OF THE INVENTION

The present invention relates to the field of laser scanning imaging systems such as the type used in microscopy, and more particularly concerns a method and a system for extending and possibly adjusting the depth of field in optical laser scanning microscopy.

BACKGROUND OF THE INVENTION

Progress in optical microscopy has led to the emergence of a wide range of systems for fluorescence imaging of biological samples. For example, confocal ["Microscopy apparatus", U.S. Pat. No. 3,013,467 to Minsky] and two-photon [Denk et al., "Two-Photon Laser Scanning Fluorescence Microscopy", Science vol. 48, p. 73-76 (1990)] laser scanning fluorescence microscopes having better spatial resolution than conventional wide-field microscopy are now commonly employed for imaging narrow sections of biological structures, in which features of interest are tagged with fluorescent markers. Both confocal and two-photon laser microscopes can provide depths of field of the order of only a few micrometers ($\mu m$) [Zipfel et al., "Nonlinear magic: multiphoton microscopy in the biosciences", Nature Biotechnology vol. 21, p. 1369-1377 (2003)], which leads to excellent optical sectioning capabilities. This feature of laser scanning microscopy allows for the acquisition of multiple in-focus images of thin sections located at selected depths within a sample, the combination of which enabling three-dimensional imaging of thick samples.

In laser scanning fluorescence microscopy for biological applications, a laser beam is generally focused by an objective lens to a diffraction-limited spot size inside or on the surface of a biological specimen. Single-photon (e.g. confocal), two-photon or multiphoton induced fluorescence is generated at the diffraction-limited focal volume. Scattered and reflected laser light, as well as fluorescent emission light from the sample, are re-collected by the objective lens and may be separated by beam splitters. The beam splitters are typically configured to selectively transmit or reflect fluorescence emission while attenuating the scattered and reflected laser light. High-sensitivity photodetectors can be used to detect the selectively filtered fluorescence emission and transform the detected light into an electrical signal, which may be recorded by a computer. By raster scanning the fluorescent sample in three dimensions such as, for example, by using a galvanometer-driven x-y scanner and a piezo-objective z-driver, a volumetric image of the sample may be obtained on a pixel-by-pixel basis, wherein the brightness of each pixel corresponds to the relative intensity of detected light emanating from an elementary volume of the sample. Therefore, imaging a sample whose thickness is larger than the depth of field generally involves acquiring a stack of two-dimensional images at different depths, and adding or averaging these images numerically [Burvall, "Axicon imaging by scalar diffraction theory", PhD thesis, Royal Institute of Technology, Sweden (2004)]. By way of example, FIG. 1 (PRIOR ART) shows an example of a laser-scanning microscope used for two-photon excited fluorescence.

Although confocal and two-photon laser scanning microscopies share many similarities, two-photon absorption has evolved, due in part to the widespread availability of ultrashort and intense laser pulses, into a particularly powerful tool for vital imaging of biological systems. Two-photon laser scanning microscopy has also alleviated some of the drawbacks of confocal microscopy. In particular, two-photon microscopy provides three-dimensional optical sectioning with limited emission of background fluorescence from outside the plane of focus and reduced photobleaching and photodamage. As a result, this technique can yield improved tissue penetration, as compared to confocal microscopy, while also being less phototoxic to live specimens. Moreover, the non-linear nature of the two-photon process provides intrinsic optical sectioning, which is achieved without a confocal pinhole.

Yet, despite the benefits of the optical sectioning capabilities and the increased spatial resolution achievable by two-photon laser scanning microscopy, the point illumination principle used in this technique reduces the acquisition speed for thick or bulk samples, since a stack of images taken at different depths must be acquired and added. In other words, the maximum acquisition speed of an extended depth-of-field image is therefore N times slower than the acquisition of one two-dimensional image at a single depth, where N is the number of two-dimensional images in the stack. Optical sectioning thus leads to a loss of temporal resolution which may not be suitable when investigating dynamic biological processes for which temporal resolution may be more important than axial resolution. For example, when dynamic interactions between neurons tagged with fluorescent markers are studied, the time between activation of two neuronal cells located at different depths within a specimen may need to be observed [Zipfel et al., "Nonlinear magic: multiphoton microscopy in the biosciences", Nature Biotechnology vol. 21, p. 1369-1377 (2003); König, "Multiphoton microscopy in life sciences", Journal of Microscopy vol. 200, p. 83-104 (2000)]. Conventional two-photon laser scanning microscope thus requires scanning a sample along several transverse places, each at a different depth within the sample, in order to cover the whole region of interest, thereby significantly increasing acquisition time and reducing temporal resolution.

In this context, various approaches have been proposed to increase the depth of field of laser scanning microscopes. These depth-of-field-extension methods may be classified into four categories, which are considered in greater detail below.

The first method involves focus elongation through added spherical aberration, as described, for example, in the following documents: Burvall et al., "Simple lens axicon", Applied Optics vol. 43, p. 4838-4844 (2004); and "System and methods for thick specimen imaging using a microscope based tissue sectioning device", U.S. Pat. Appl. Pub. No. 2009/0091566 to Turney and Sheard. While the spherical aberration method effectively allows for an increase of the depth of field, the resulting focal spot size varies along the propagation axis. Therefore, image resolution is not constant across the thickness of the sample.

The second method involves wavefront coding with a phase mask followed by digital processing, as described, for example, in the following documents: Tucker et al., "Extended depth of field and aberration control for inexpensive digital microscope systems", Optics Express vol. 4, p. 467-474 (1999); "Extended depth of field optical systems", U.S. Pat. No. 7,218,448; and "Method, apparatus and system for extending depth of field (DOF) in a short-wavelength microscope using wavefront encoding", U.S. Pat. Appl. Pub. No. US 2008/0240347 to Bloom. In the wavefront coding approach, the excitation beam is distorted and the images thus acquired are blurry and must be treated by digital processing before obtaining the effective resolution. The advantage of this method relies mainly on its compatibility with wide-field microscopy. However, it cannot be applied to laser scanning microscopy and relies on numerical post-treatment.

The third method involves a rapid variation of the focal length, as described, for example, in the following documents: Olivier et al., "Two-photon microscopy with simultaneous standard and extended depth of field using a tunable acoustic gradient-index lens", *Optics Letters* vol. 34, p. 1684-1686 (2009); Smith et al. "Extended depth-of-field microscopy" *Proceedings of SPIE* vol. 7570, p. 75700S (2010); Botcherby et al., "Real-time extended depth of field microscopy", *Optics Express* vol. 16, p. 21843-21848 (2008); "Extended depth of focus microscopy", Inter. Pat. Appl. Pub. No. WO 2004/075107 to Dresser; and "Apparatus and method for extended depth of field imaging", U.S. Pat. Appl. No. 2008/0089598 to George and Chi. The focal depth variation technique consists in rapidly changing the focal plane while acquiring each pixel. The depth of field extension is limited by defocus aberration, which degrades image resolution for large variations in depth. Furthermore, in some cases, the acquired images are blurry and must be treated by digital processing before obtaining the effective resolution.

Finally, the fourth method involves the generation of a non-diffracting beam, as described, for example, in the following documents: Dufour et al., "Two-photon excitation fluorescence microscopy with a high depth of field using an axicon", *Applied Optics*, vol. 45, p. 9246-9252 (2006); Arimoto, "Imaging properties of axicon in a scanning optical system", *Applied Optics* vol. 31, p. 6653-6657 (1992); "Laser scanning optical system using an axicon", Eur. Pat. No. 0 627 643 to Ichie; "Laser scanning optical system and laser scanning optical apparatus" U.S. Pat. No. 5,583,342 to Ichie; Botcherby et al., "Scanning two photon fluorescence microscopy with extended depth of field", *Optics Communications* vol. 268, p. 253-260 (2006); and "High resolution imaging devices with wide field and extended focus", U.S. Pat. Appl. No. 2011/0205352 to Pavani et al.

Non-diffracting beams, such as Bessel beams and Mathieu beams, are known to retain their transverse profile while propagating, thereby allowing for lateral image resolution to be maintained throughout the thickness of the sample. In laser scanning microscopy, an interesting type of non-diffracting beam is the Bessel beam whose transverse intensity profile follows a zero-order Bessel function of the first kind characterized by an intense central peak with low-intensity side lobes. While the ideal Bessel beam extends indefinitely in the transverse plane, thus preventing any physical realization of such a beam, it may be experimentally generated to a close approximation by adding thereto a Gaussian envelope. This yields a so-called "Bessel-Gauss beam", which retains most of the non-diffractive nature of the central peak of the ideal Bessel beam.

Methods have been presented for producing Bessel-Gauss beams as a way to increase the depth of field in laser scanning microscopy and may be classified depending on the type of optical elements, for example refractive or diffractive, employed for their generation.

On the one hand, an axicon can be a conical lens, which is the simplest refractive optical element capable of generating Bessel-Gauss beams [McLeod, "The axicon: a new type of optical element", *Journal of the Optical Society of America*, vol. 44, p. 592-597 (1954)]. In 2006, Dufour et al. [Dufour et al., "Two-photon excitation fluorescence microscopy with a high depth of field using an axicon", *Applied Optics*, vol. 45, p. 9246-9252 (2006)] proposed to replace the objective lens of a two-photon laser scanning microscope by a large-angle conical lens so as to illuminate the sample with Bessel-Gauss beams having an extended depth of field. However, limitations of this approach include a slow scan rate arising from the need to displace the axicon mechanically, an absence of a proper working distance, a less-than-optimal fluorescence collection, and difficulties in fabricating defect-free large-angle conical lenses and in adjusting the depth of field.

Arimoto et al. [Arimoto, "Imaging properties of axicon in a scanning optical system", *Applied Optics* vol. 31, p. 6653-6657 (1992)] describe a laser scanning optical system that incorporates a conical lens to provide an extended depth of focus. The beam-shape characteristics and control of the resulting Bessel beam as well as aberration effects arising from off-axis illumination are experimentally studied. However, scanning the excitation beam in the plane of the sample is considered only along one axis and the system does not include collection and detection of fluorescence. Moreover, while providing a laser scanning microscope based on their design considered, several problems are anticipated, most notably optical aberrations at large scanning angles and low-contrast images due to the side lobes of the Bessel beam.

In another approach, Ichie ["Laser scanning optical system using an axicon", Eur. Pat. No. 0 627 643 to Ichie; "Laser scanning optical system and laser scanning optical apparatus" U.S. Pat. No. 5,583,342 to Ichie] introduced two identical conical lenses in a laser scanning microscope. The conical lenses are arranged such that apexes thereof are opposed forward or backward to each other. The two conical lenses produce an annular laser beam which then passes through the objective lens of the microscope, thus illuminating the sample with a Bessel beam. However, this system poses severe constraints on the mechanical alignment and the fabrication tolerance error of the conical lenses.

In a further approach, phase-modulating diffractive optical elements have also been proposed in order to increase the depth of field in two-photon laser scanning microscopy. In particular, Botcherby et al. [Botcherby et al., "Scanning two photon fluorescence microscopy with extended depth of field", *Optics Communications* vol. 268, p. 253-260 (2006)] used a binary phase-only diffractive optical element to simulate the linear superposition of a positive and a negative axicon and thus convert a laser beam into an annular beam. As in Ichie ["Laser scanning optical system using an axicon", Eur. Pat. No. 0 627 643 to Ichie; "Laser scanning optical system and laser scanning optical apparatus" U.S. Pat. No. 5,583,342 to Ichie], the annular beam is then converted into a Bessel beam at the sample after passing through the objective lens of the microscope. However, while this system can allow for an increase of the axial extent of the beam illuminating the sample without compromising the lateral resolution, the annular beam thus generated must be spatially filtered to remove higher orders of diffraction. This filtering process leads to a loss of 25% of the optical power and requires two additional lenses. In this regard, it should be emphasized that because Bessel-Gauss beam gradually spread its power as a beam travels along the propagation axis, the intensity of the signal scales inversely to the distance traveled by the beam. For at least this reason, optimizing the power throughput of the microscope and adjusting the depth of field to the thickness of the sample becomes desirable in extended depth-of-field microscopy methods.

In light of the above, a need in the art exists for a system and method capable of providing an extended and adjustable depth of field in laser scanning microscopy with reduced loss of optical power and lateral resolution, while also alleviating at least some of the drawbacks of the prior art.

SUMMARY OF THE INVENTION

According to an aspect of the invention, there is provided a laser scanning imaging system for obtaining an extended-depth-of-field image of a volume of a sample. The laser scanning imaging system includes:
  a laser module configured to generate an input laser beam;
  a beam shaping module provided in a path of the input laser beam, the beam shaping module including:
    an axicon formed and disposed for converting the input laser beam into an intermediate non-diffracting beam; and
    a Fourier-transform lens formed and disposed for converting the intermediate non-diffracting beam into an intermediate annular beam; and
  an imaging module including:
    an objective lens formed and disposed so as to receive the intermediate annular beam and convert the same into an excitation non-diffracting beam for projection onto the volume of the sample, the excitation non-diffracting beam having a depth of field and a transverse resolution together defining a three-dimensional excitation region; and
    a detecting assembly for collecting electromagnetic radiation from the excitation region and for obtaining therefrom one of a plurality of pixels of the extended-depth-of-field image of the volume of the sample; and
  a two-dimensional scanning module for scanning the excitation non-diffracting beam over the sample so as to build the extended-depth-of-field image of the volume of the sample from the plurality of pixels thereof.

According to another aspect of the invention, there is provided a method for obtaining an extended-depth-of-field image of a volume of a sample using laser scanning imaging. The method includes the steps of:
  a) generating an input laser beam;
  b) converting the input laser beam into an excitation non-diffracting beam, including the substeps of:
    i) converting the input laser beam into an intermediate non-diffracting beam by causing the input laser beam to pass through an axicon;
    ii) converting the intermediate non-diffracting beam into an intermediate annular beam by causing the intermediate non-diffracting beam to pass through a Fourier-transform lens; and
    iii) converting the intermediate annular beam into the excitation non-diffracting beam by causing the intermediate annular beam to pass through an objective lens; and
  c) projecting the excitation non-diffracting beam onto the volume of the sample, the excitation non-diffracting beam having a depth of field and a transverse resolution together defining a three-dimensional excitation region;
  d) collecting electromagnetic radiation from the excitation region and obtaining therefrom one of a plurality of pixels of the extended-depth-of-field image of the volume of the sample; and
  e) scanning the excitation non-diffracting beam over the sample along two-dimensions so as to build the extended-depth-of-field image of the volume of the sample from the plurality of pixels thereof.

According to another aspect of the invention, there is provided a method for extending a depth of field of a laser scanning imaging system including:
  a laser module configured to generate an input laser beam;
  an imaging module including an objective lens for projecting the input laser beam onto a volume of a sample and a detecting assembly for collecting electromagnetic radiation from the volume of the sample; and
  a two-dimensional scanning module for scanning the input laser beam over the sample.

The method includes the step of providing a beam shaping module in a path of the input laser beam between the laser module and the scanning module. The beam shaping module includes:
  an axicon formed and disposed for converting the input laser beam into an intermediate non-diffracting beam; and
  a Fourier-transform lens formed and disposed for converting the intermediate non-diffracting beam into an intermediate annular beam and for directing, via the scanning module, the intermediate annular beam onto the objective lens for conversion of the same into an excitation non-diffracting beam, the excitation non-diffracting beam having an extended depth of field that defines the depth of field of the laser scanning imaging system.

Other features and advantages of the present invention will be better understood upon reading of preferred embodiments thereof with reference to the appended drawings.

DESCRIPTION OF PREFERRED EMBODIMENTS OF THE INVENTION

Figure 1:
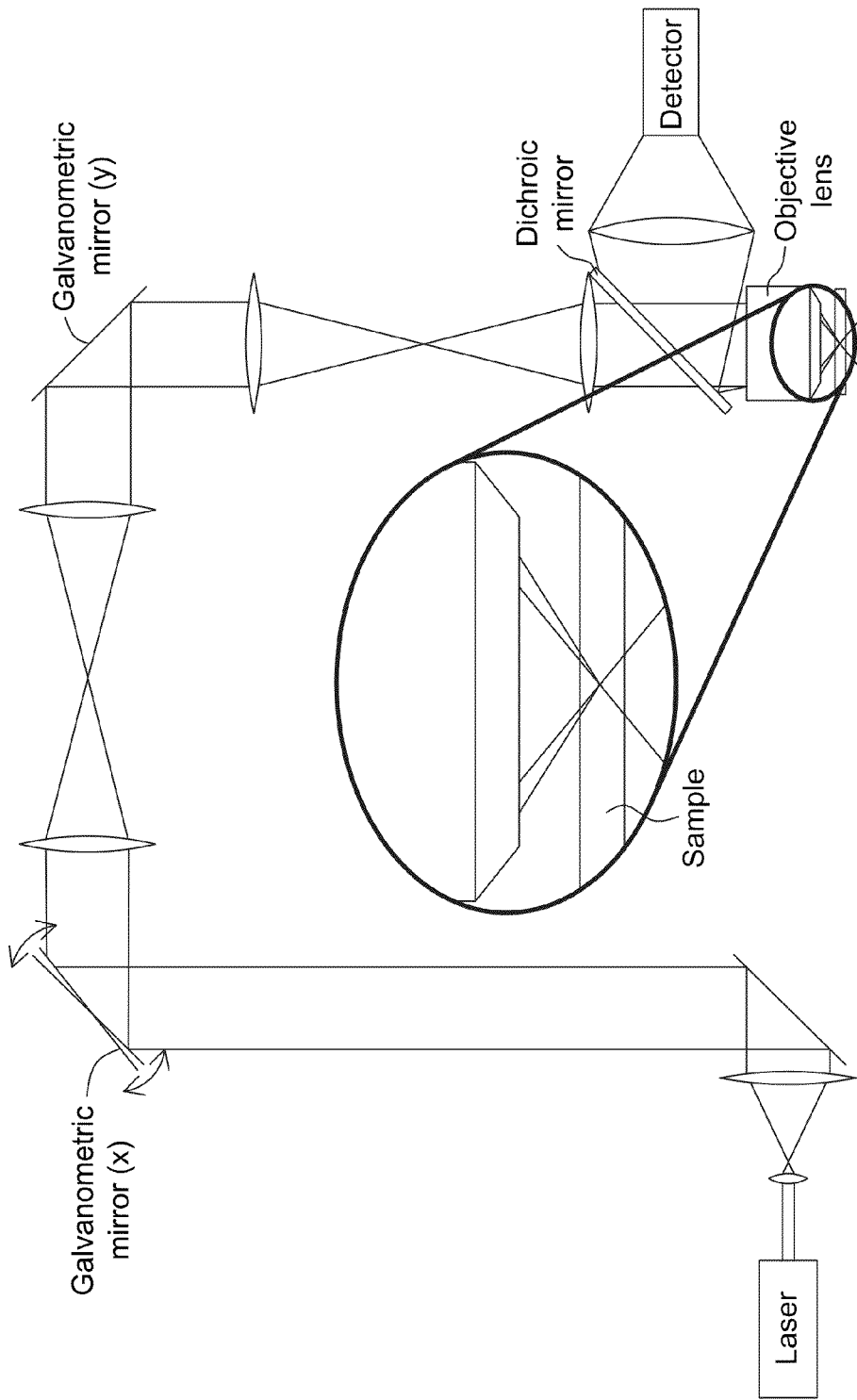
FIG. 1 (PRIOR ART) is schematic representation of laser scanning microscope configured for two-photon microscopy.

In the following description, similar features in the drawings have been given similar reference numerals and in order to weigh down the figures, some elements may not be referred to on some figures if they were already identified in preceding figures. It should also be understood herein that the elements of the drawings are not necessarily drawn to scale and that the emphasis is instead being placed upon clearly illustrating the elements and structures of the present embodiments.

The present invention generally relates to a laser scanning imaging system and method for obtaining an image of a volume of a sample, wherein the image has an extended depth of field, that is, axial resolution, compared to standard systems and methods. The system and method according to embodiments of the present invention generally involve converting an input laser beam into an excitation non-diffracting beam in a stepwise manner, and projecting the excitation non-diffracting beam thus obtained onto the sample. This excitation non-diffracting beam has a depth of field and a transverse resolution that together define a three-dimensional excitation region of a volume of the sample.

Embodiments of the laser scanning imaging system include, inter alia, a beam shaping module and an imaging module having an objective lens. The beam shaping module includes an axicon and a Fourier-transform lens that combine to generate, from the input laser beam, an intermediate annular beam. The objective lens receives the intermediate annular beam and converts the same into an excitation non-diffracting beam for projection onto the sample.

As will be described in greater detail below, the provision of such a beam shaping module in embodiments of the laser scanning imaging system allows for an increase of the depth of field and for the acquisition of an extended-depth-of-field image of a volume of a sample from a single two-dimensional scan thereof. As a result, embodiments of the present invention may also improve the temporal resolution of laser scanning microscopes, that is, the time required to acquire a series of image data of a volume of interest of a sample. Embodiments of the invention may thus be particularly well adapted for investigating microscopic characteristics and dynamic behaviors in biological tissues. Moreover, embodiments of the present invention involve reduced or negligible loss of optical power and no loss of transverse resolution, offer an adjustable depth of field, and may be readily integrated into most commercial laser scanning microscopy systems.

Examples of microscopic systems which may benefit from the present invention include, without being limited to, a confocal microscope, a two-photon microscope, a multiphoton microscope, a second-harmonic imaging or third-harmonic imaging microscope, a reflectance microscope, a coherent anti-Stokes Raman scattering system, a stimulated Raman scattering system, a sum-frequency generation system, and the like.

Laser Scanning Imaging System

Figure 5A:
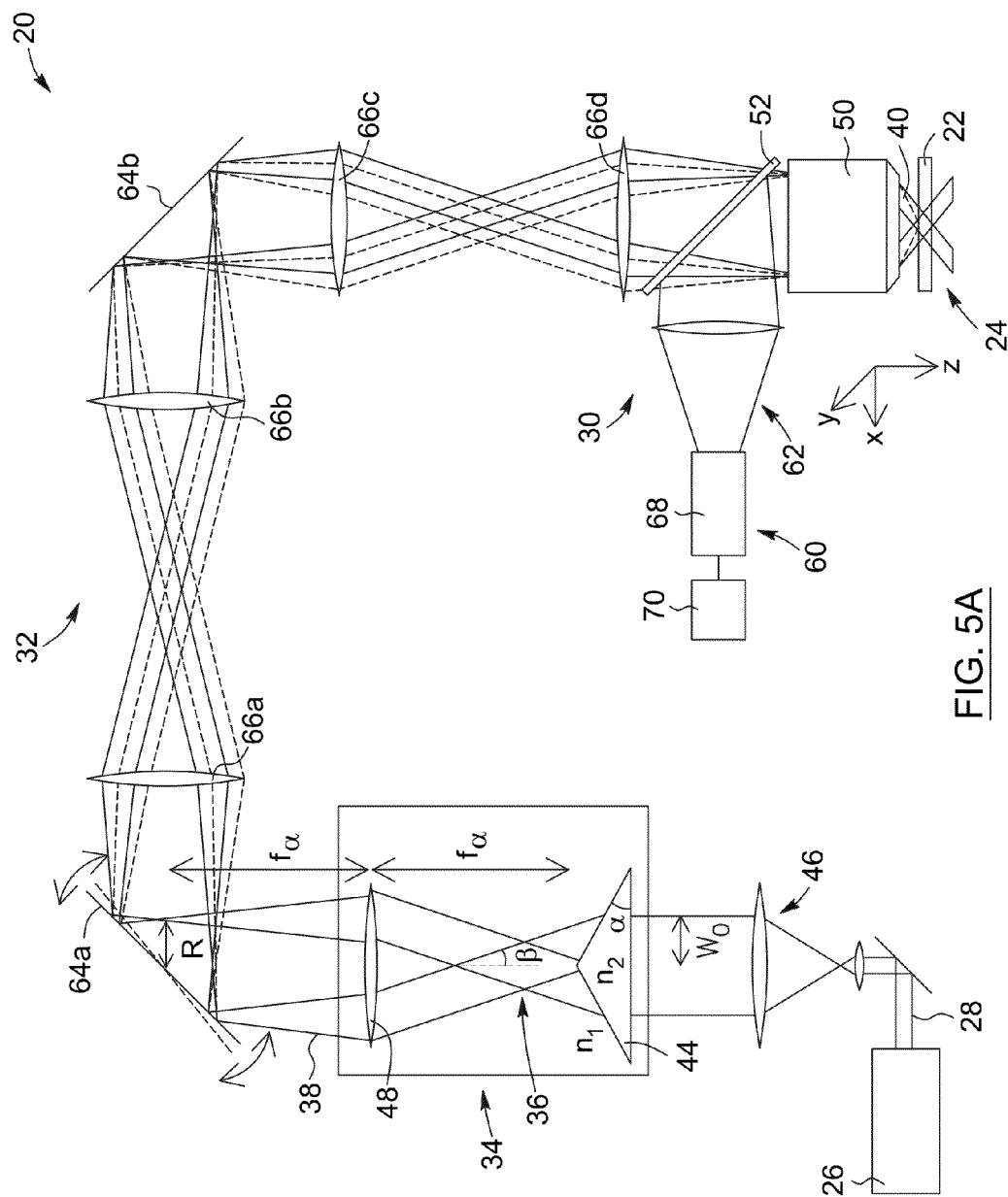
FIG. 5A is a schematic representation of a laser scanning imaging system for obtaining an extended-depth-of-field image of a volume of a sample, in accordance with an embodiment of the invention configured for two-photon microscopy.

In accordance with an aspect of the invention, a laser scanning imaging system 20 is provided, an embodiment of which is shown in FIG. 5A. The laser scanning imaging system 20 can be used for obtaining an extended-depth-of-field image of a volume 22 of a sample 24. It will be understood that depending on the intended applications of the laser scanning imaging system and on the dimensions of the sample, the term "volume of a sample" may refer to the whole sample or to a portion thereof.

As used herein, the expression "depth of field" or "axial resolution" is understood to refer to the range of distances along the optical axis within which objects points appear to be sharply in focus in the image plane. One skilled in the art will understand that in practice, the definition of the depth of field may depend on the context of a particular embodiment. For example in conventional microscopy, it is customary to define the depth of field as twice the Rayleigh length which, in the field of laser science, corresponds to the distance from the beam waist along the propagation direction where the beam cross-sectional area doubles. Furthermore, in the context of fluorescence imaging of biological samples, the depth of field may be interpreted as the on-axis distance along which the point spread function (PSF) of the excitation signal is intense enough to produce a contrasted fluorescence signal.

Throughout the present description, the expression "extended depth of field" is understood to refer to a depth of field that is larger than the depth of field typically achievable using conventional laser scanning microscopy. For example, in the case of two-photon laser scanning microscopy, a depth of field of the order of 150 µm could be achieved in some embodiments of the invention, which is considerably larger than the depth of field obtained using conventional two-photon laser scanning microscopes, which is typical of the order of a few micrometers. The system according to this aspect of the invention can thus provide an extended-depth-of-field volumetric image of a relatively thick sample in a single two-dimensional scan thereof.

It will be understood that any sample that can be studied with conventional laser scanning imaging techniques may benefit from the system according to this aspect of the invention for obtaining extended-depth-of-field volumetric images thereof. In some embodiments, the sample is a biological specimen, which can include, without being limited to, endogenous fluorescent molecules suitable for laser scanning fluorescence imaging, intrinsic signals detectable through other imaging modalities (e.g. second or third harmonic generations and Raman scattering), or exogenous fluorophores or contrast agents, that is, molecules designed to label biological structures and monitor biological functions. Non-limiting examples of biological specimens that can be studied with embodiments of the invention include tissues, cells and subcellular structures, living or not, while non-limiting examples of biological functions include ion or voltage fluctuations, dynamic reshaping of cellular structures and cell migration.

Still referring to FIG. 5A, the laser scanning imaging system 20 may be built similarly to standard laser scanning microscopy systems, in that it generally includes a laser module 26 configured to generate an input laser beam 28, an imaging module 30 and a two-dimensional scanning module 32. It will be understood that the laser module 26 and the imaging module 30 may be optically linked through optical fibers (not shown) or free space propagation. The laser module 26, imaging module 30 and scanning module 32 together define a microscope which, in the illustrated embodiment, is a two-photon laser scanning fluorescence microscope.

Of course, it will be understood that the particular configuration for the imaging and scanning modules 30, 32 shown in FIG. 5A and described below is by way of example only. In practice, the imaging and scanning modules 30, 32 may be embodied by a number of other components and configurations. For example, in other embodiments, rather than being configured for two-photon laser scanning microscopy, the system 20 may be configured for higher order multi-photon (that is, more than two photons) scanning microscopy, confocal laser scanning microscopy, or any other type of laser scanning microscopes or imaging systems, such as those listed above, without departing from the scope of the invention.

Laser Module

The laser module 26 illustrated schematically in FIG. 5A may be embodied by any appropriate device or combination of devices able to generate an input laser beam 28 suitable for probing the volume 22 of the sample 24 in the context of the present system 20. Depending on the intended application, the laser module 26 may include a gas laser, an electrically-pumped semiconductor laser, an optically-pumped solid-state laser, an optical fiber laser, a solid state amplification system, a mode-locked titanium-sapphire (Ti:sapphire) laser, and the like. It is to be emphasized that the laser module 26 according to embodiments of the invention may be operated in both continuous-wave and pulsed regimes. Furthermore, for non-linear laser scanning microscopy applications involving unchirped short pulses, a dispersion compensator could be added to the system 20 after the laser module 26.

In the present description, the term "laser beam" is understood to refer to a high-intensity, spatially-coherent and nearly monochromatic beam of electromagnetic radiation. Depending on the intended application, the electromagnetic radiation forming the input laser beam 28 may include photons having energies lying in any appropriate portion region of electromagnetic spectrum, including the visible, infrared and ultraviolet frequency ranges. As known in the art, the input laser beam 28 may be characterized by several optical characteristics such as, for example, its wavelength, frequency, intensity, polarization, and size. Preferably, the input laser beam 28 is a pulsed laser beam, which may be described in terms of its pulse duration, repetition rate, spatial and spectral profiles, and the like. It will be understood, however, that the input laser beam 28 may have any optical characteristics suitable for a given application.

For example, in the embodiment of FIG. 5A, the laser module 26 is configured to generate, as the input laser beam 28, a Gaussian laser beam whose transverse electrical field $E(r) \sim \exp[-r^2/w^2(z)]$ and intensity distribution $I(r) \sim \exp[-2r^2/w^2(z)]$ are well approximated by Gaussian functions, where r is the radial coordinate in a plane transverse to the propagation axis of the beam and $w(z)$ is width of the input laser beam 28.

Beam Shaping Module

Still referring to FIG. 5A, the laser scanning imaging system 20 also includes a beam shaping module 34 provided in a path of the input laser beam 28, between the laser module 26 and the imaging module 30. Depending on the intended application, the beam shaping module 34 may be retrofitted into an existing laser scanning imaging system 20 or an extended-depth-of-field imaging system 20 may alternatively be built with the beam shaping module 30 already incorporated therein.

As will be described in greater detail below, the beam shaping module 34 allows for the conversion of the input laser beam 28 into an intermediate non-diffracting beam 36 and further into an intermediate annular beam 38. As will also be described below, the intermediate annular beam 38 is received inside the imaging module 30, where it can be converted into an excitation non-diffracting beam 40 having an extended depth of field.

In some embodiments, the laser scanning imaging system may be designed so as to include two distinct light paths. In one of the paths, the input laser beam outputted by the laser module passes through the beam shaping module, while in the other path, the input laser beam generated by the laser module reaches the imaging module without passing through the beam shaping module.

Figure 6:
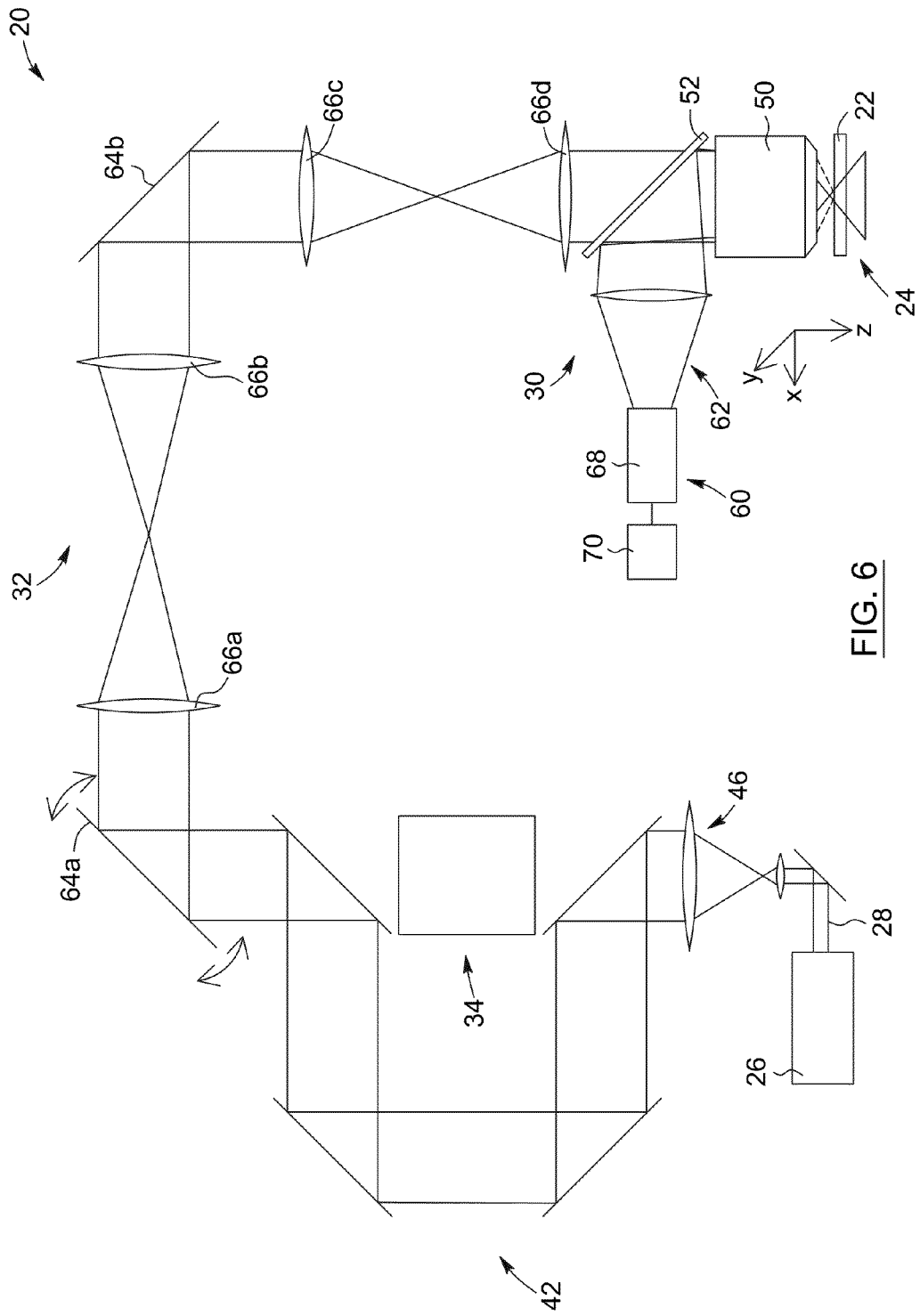
FIG. 6 is a schematic representation of a laser scanning imaging system for obtaining an extended-depth-of-field image of a volume of a sample, in accordance with another embodiment of the invention configured for two-photon microscopy, wherein the system includes a switching device.

Referring now to FIG. 6, an embodiment of the laser scanning imaging system 20 is shown that includes a switching module 42 disposed between the laser module 26 and the beam shaping module 34. The switching module 42 is operable between a first mode and a second mode. On the one hand, in the first mode, the switching module 42 directs the input laser beam 28 onto the beam shaping module 34. On the other hand, in the second mode, illustrated in FIG. 6, the switching module 42 directs the input laser beam 28 onto the imaging module 30 by bypassing the beam shaping module 34. In the embodiment of FIG. 6, the switching module 42 is embodied by a set of deflecting mirrors, but any other suitable device or combinations of devices able to selectively steer the input laser beam 28 along different optical paths may be used without departing from the scope of the present. It will be understood that the provision of a switching module in embodiments of the invention allows for the laser scanning imaging system to be operated selectively in either an extended-depth-of-field mode, wherein the input laser beam passes through the beam shaping module, or in a conventional mode, wherein the input laser reaches the imaging module without passing through the beam shaping module.

Referring back to FIG. 5A, the beam shaping module 34 first includes an axicon 44 formed and disposed for converting the input laser beam 28 into an intermediate non-diffracting beam 36. As used herein, the term "axicon" generally refers to a refractive optical element with a rotationally symmetric surface, which has the property that a point source on its axis of revolution is imaged as a line defining a focal zone along the axis of revolution.

In the embodiment of FIG. 5A, the axicon 44 is embodied by a conical lens formed by the association of a plane surface and a conical surface and characterized by its refractive index $n_2$, which depends on its composition, and by the angle α between its plane and conical surfaces. However, other refractive axicons able to produce non-diffracting beams may be used in other embodiments such as, for example, logarithmic axicons [Golub et al., "Characterization of a refractive logarithmic axicon", *Optics Letters*, vol. 35, p. 2828-2830 (2010)] and Fresnel axicons [Gourley et al., "First experimental demonstration of a Fresnel axicon", Photonics North 2008, Vallée et al., editors, *Proceedings of the SPIE*, vol. 7099, p. 7099D (2008)].

Axicons can be used to transform a Gaussian beam into an approximation of a Bessel beam, which is a type of non-diffracting beam corresponding to a propagation invariant solution of the Helmholtz wave equation in circular cylindrical coordinates. Other exact non-diffracting solutions of the Helmholtz wave equation exist such as, for example, Mathieu beams in elliptic coordinates and parabolic beams in parabolic coordinates.

Throughout the present description, the term "non-diffracting beam" refers to a beam of electromagnetic radiation whose transverse intensity profile remains substantially constant over a relatively long distance along the beam propagation axis. A non-diffracting beam may thus propagate over a large range without experiencing significant divergence. For at least this reason, Bessel beams are of interest for many applications which could benefit from an extended depth of field.

Figure 2:
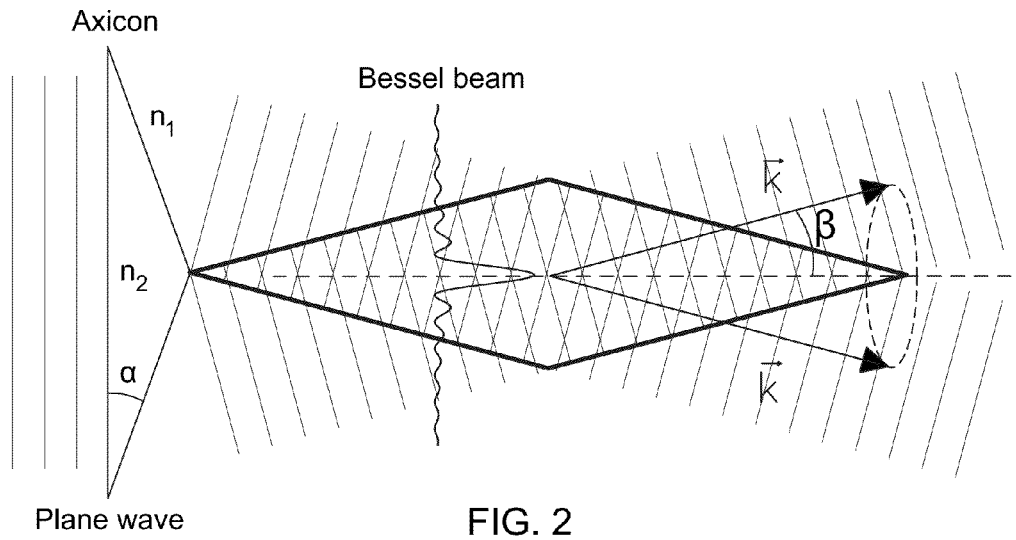
FIG. 2 (PRIOR ART) is a schematic representation of a Bessel beam as a superposition of a continuum of uniform plane waves whose wave vectors form a cone of angle β.

Bessel beams are beams of electromagnetic radiation whose transverse intensity profile describes a Bessel function of the first kind and order zero $J_0(x)$. As known in the art, the function $J_0(x)$ exhibits an intense central lobe surrounded by an infinite set of concentric rings whose intensity decreases as a function of radial distance from the propagation axis. As shown in FIG. 2 (PRIOR ART), a Bessel beam may be represented as a superposition of a continuum of uniform plane waves whose wave vectors k lie on a cone of angle β given by $$\beta = \sin^{-1}\left(\frac{n_2}{n_1}\sin\alpha\right) - \alpha, \quad (1)$$

where $n_1$ is the refractive index of the medium surrounding the axicon 44, and $n_2$ and α are respectively the refractive index of the axicon 44 and the angle between the flat and conical surfaces of the axicon 44 embodied by a conical lens. Because of its non-diffracting nature, the central lobe of an ideal Bessel beam has a constant radius, regardless of its distance from the axicon. In other words, the transverse intensity profile of an ideal Bessel beam does not change under free space propagation. However, as will be understood by one of ordinary skill in the art, an ideal non-diffracting beam (e.g. a Bessel beam) is not physically realizable as it would have, in theory, infinite extent and energy. In practice, a more accurate example of a non-diffractive beam produced by an axicon is a Bessel-Gauss beam, as will now be described.

Figure 3:
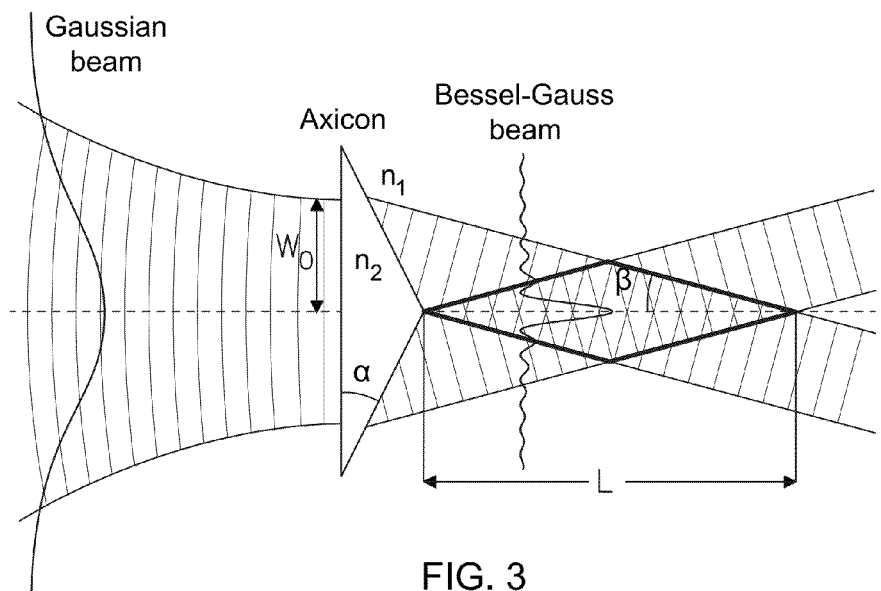
FIG. 3 (PRIOR ART) is a schematic representation of the conversion of a Gaussian beam into a Bessel-Gauss beam achieved by passing the Gaussian beam through an axicon.

Referring to FIG. 3 (PRIOR ART), a schematic ray-trace representation is depicted that illustrates how a Bessel-Gauss beam may be obtained by illuminating an axicon with a Gaussian beam. It is seen that a Bessel-Gauss beam corresponds to the superposition of a continuum of Gaussian beams whose wave vectors form a cone of angle β with respect to the propagation axis.

Referring back to the exemplary embodiment shown in FIG. 5A, and as mentioned above, the laser module 26 is configured to generate the input laser beam 28 as a Gaussian beam, which is received by the axicon 44 of the beam shaping module 34. In the illustrated embodiment, the axicon 44 is formed and disposed to convert this Gaussian beam into the intermediate non-diffractive beam 36, which, in this case, is a Bessel-Gauss beam, such as that shown in FIG. 3 (PRIOR ART).

An expression for the intensity distribution near the optical axis of a Bessel-Gauss beam may be obtained from a stationary phase approximation of the Fresnel diffraction integral. This leads to $$I(r, z) = I_0 \frac{4\pi^2 \beta^2 z}{\lambda} \exp\left(\frac{-2\beta^2 z^2}{w_0^2}\right) J_0^2\left(\frac{2\pi r \beta}{\lambda}\right), \quad (2)$$

where $I_0$ is the intensity at the center of the Gaussian input laser beam 28, β is the deflection angle produced by the axicon 44 as given by Equation (1), λ is the wavelength of radiation, $w_0$ is the width of the input laser beam 28 incident on the axicon, z is the coordinate along the propagation axis, and r is the radial coordinate in a plane transverse to the propagation axis.

By looking at Equation (2), one of ordinary skill in the art will recognize that the transverse intensity distribution of the intermediate non-diffracting beam 36 assumes, in this embodiment, the form of a Bessel function of the first kind and order zero and is invariant along the propagation axis z of the beam. As a result, the Bessel-Gauss of Equation (2) may be a suitable exemplary non-diffracting beam whose transverse resolution is controlled by the deflection angle β of the axicon 44.

In embodiments where the intermediate non-diffracting beam produced by the axicon has a Bessel-Gauss profile, the term "transverse resolution" of the intermediate non-diffracting beam is understood to refer to size of the central lobe of its central lobe, and more specifically to the radius r=ρ of the first zero of the Bessel function of the first kind and order zero, which is given by:

$$\rho = \frac{2.4048\lambda}{2\pi\beta}. \quad (3)$$

It is to be noted, as will be understood by one of ordinary skill in the art, that this value for the transverse resolution ρ also corresponds to the full width at half maximum (FWHM) of the signal PSF for two-photon fluorescence in the transverse plane.

Another useful parameter that may be extracted from Equation (2) is the depth of field L. Throughout the present description, the depth of field L is mathematically defined as the FWHM of the signal PSF along the optical axis, which is directly proportional to I(r=0, z) in single-photon (i.e. confocal) fluorescence and to the squared intensity $I^2$(r=0, z) in two-photon fluorescence. Accordingly, the depth of field can be expressed as follows:

$$L = C\left(\frac{w_0}{\beta}\right), \quad (4)$$

where the constant C has a value of 0.8 for single-photon fluorescence and 0.58 for two-photon fluorescence.

By looking at Equation (4), one of ordinary skill in the art will recognize that in embodiments of the laser scanning imaging system 20 that allows for a control of the width $w_0$ of the Gaussian input laser beam 28, the depth of field L of the Bessel-Gauss intermediate non-diffracting beam 36 could be varied while keeping constant its transverse resolution ρ, which depends only on λ and β [see, e.g. Equation (2)]. Still referring to FIG. 5A, the laser scanning imaging system 20 may further include a beam-width control module 46 provided in the path of the input laser beam 28 and disposed between the laser module 26 and the beam shaping module 34. It will be understood that the beam-width control module 46 can act as a beam expander or reducer for controlling the diameter or the magnification of the input laser beam 28 before it reaches the beam shaping module 34. In some embodiments, the beam-width control module 46 may be embodied by a telescope, while in other embodiments, the beam-width control module 46 may be embodied by an iris disposed between the laser module 26 and the axicon 44 that controls the width of the input laser beam 28 as it is transmitted thereacross.

It will be understood, however, that as the depth of field L of the intermediate non-diffracting beam 36 is increased, its peak intensity decreases accordingly. Still referring to the embodiment of FIG. 5A, if one considers that the total power of the Gaussian input laser beam 28 is $P=I_0\pi w_0^2/2$, then substituting P and $L=C(w_0/\beta)$ into Equation (2) yields the following equation for the on-axis intensity distribution:

$$I(r=0, z) = \frac{8\pi Pz}{\lambda}\left(\frac{C}{L}\right)^2 \exp\left(\frac{-2z^2C^2}{L^2}\right). \tag{5}$$

A partial derivative of Equation (5) with respect to z shows that the maximum intensity is proportional to P/L. Therefore, in embodiments where the laser scanning imaging system 20 is configured for two-photon fluorescence microscopy, the strength of the fluorescence signal emanating from the sample 24 decreases by a factor 4 when the depth of field L of the intermediate non-diffracting beam 36 is doubled.

Still referring to FIG. 5A, the beam shaping module 34 also includes a Fourier-transform lens 48 formed and disposed for converting the intermediate non-diffracting beam 36 into an intermediate annular beam 38. As used herein, the term "annular beam" refers to a beam whose intensity distribution defines a peripheral ring-shaped region of maximum intensity with no or negligible on-axis intensity.

The lens 48 shown in FIG. 5A is referred to as a "Fourier-transform lens" to indicate that it is used to perform a two-dimensional Fourier transform on the intermediate non-diffracting beam 36 in order to generate the intermediate annular beam 38. As is known in the art, a focusing lens can be used to perform a Fourier transform in real-time of an optical signal. It is also known in the art that Bessel and annular beams are closely related through their Fourier transform, namely that the Fourier transform in polar coordinates of an annular beam is a Bessel beam, and vice versa. Therefore, in embodiments where the intermediate non-diffracting beam 36 is a Bessel-Gauss beam, the Fourier-transform lens 48 may be used to produce the intermediate annular beam 38. It will be understood that the term "Fourier-transform lens" may refer to both individual lenses and lens systems as well as to other focusing optics. In particular, the Fourier-transform lens 48 may be embodied by a single lens, an achromat, a doublet, a triplet, an adjustable-focus lens, or a combination thereof.

Figure 4:
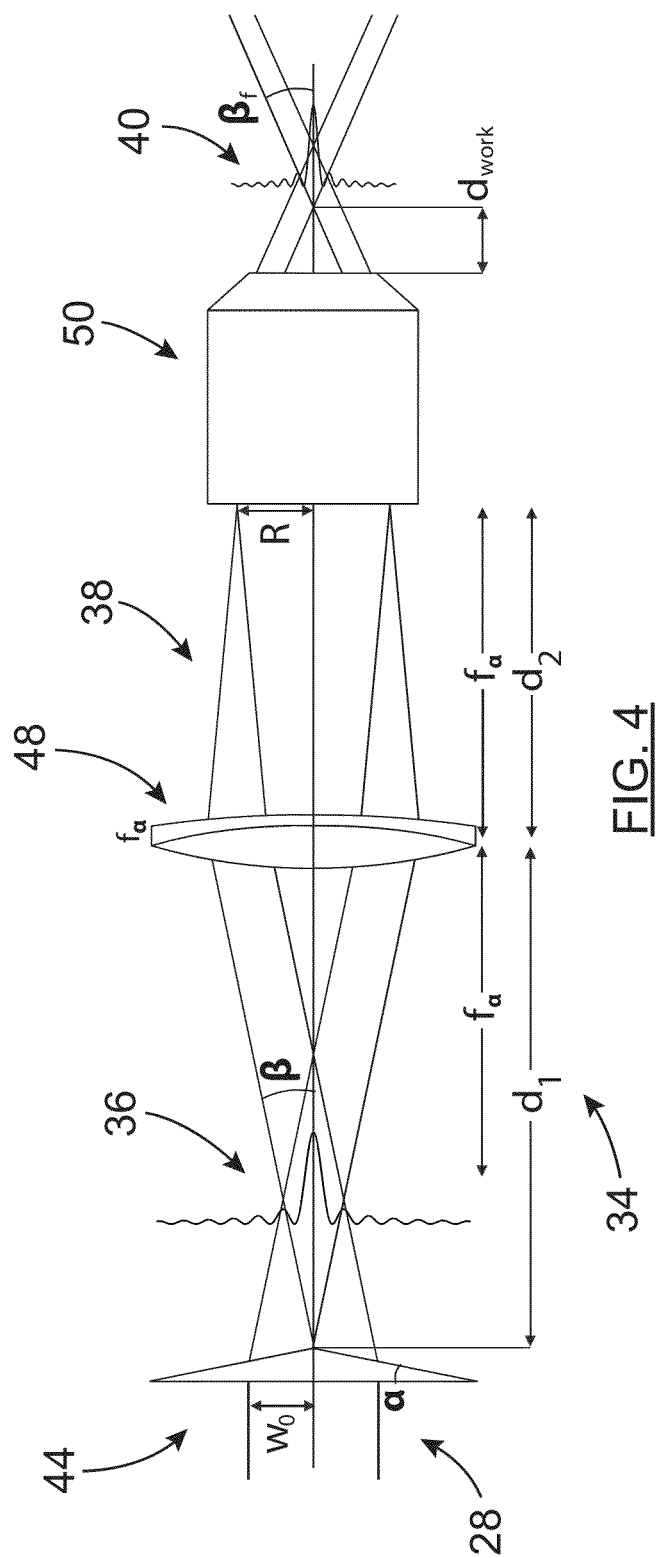
FIG. 4 is a schematic representation of a beam shaping module including an axicon and a Fourier-transform lens, in accordance with an embodiment of the invention.

Referring to FIG. 4, in some embodiments, the axicon 44 and the Fourier-transform lens 48 may be disposed relative to each other so as to be separated by a distance $d_1$ corresponding to the focal length $f_\alpha$ of the Fourier-transform lens 48. In other words, the back focal plane of the Fourier-transform lens 48 may be located within the focal zone of the intermediate non-diffracting beam zone, that is, within its depth-of field, which corresponds to the distance L indicated in FIG. 3 (PRIOR ART). However, in other embodiments, the condition $d_1=f_\alpha$ is not be fulfilled and an extended depth of field can still be achieved, in some cases more efficiently than in embodiment where the condition $d_1=f_\alpha$ is achieved. Likewise, it will be understood that the distance $d_2$ between the Fourier-transform lens 48 and the next optical element could differ from $f_\alpha$ without departing from the scope of the invention.

The Fourier-transform lens 48 will receive the intermediate non-diffracting beam 36 and perform a Fourier transform thereon to generate an intermediate annular beam 38 of radius R at the front focal plane of the Fourier-transform lens 48. In this regard, one of ordinary skill in the art will understand that the numerical aperture of the Fourier-transform lens 48 preferably corresponds to at least the same angle as the deflection angle $\beta$ (Eq. 1) produced by the axicon 44 to minimize power losses.

In some embodiments, the Fourier-transform lens 48 may have an adjustable focus. For example, in some embodiment, the adjustable-focus lens may be embodied by an electroactive polymer lens, a tunable elastic membrane lens, an adaptive liquid crystal lens, a varifocus zoom lens module, an adjustable zoom telescope module, and the like. As will described further below, providing focus adjustment capabilities to the Fourier-transform lens could allow for the control or adjustment of either or both of the depth of field and transverse resolution of the laser scanning imaging system 20 as a function of the thickness of the volume 22 without having to replace, realign or otherwise change any of its optical elements.

As described in greater detail below, the intermediate annular beam 38 produced by the Fourier-transform lens 48 is relayed through the scanning module 32 and preferably imaged onto the back focal plane of the objective lens 50 of the imaging module 30. In other words, in some embodiments, the Fourier-transform lens 48 is preferably disposed such that the front focal plane thereof is optically conjugate with the back focal plane of the objective lens 50. As used herein the two planes are said optically conjugate planes with each other if a point on a one the planes is imaged on the other one of the planes, and vice versa.

More specifically, the Fourier-transform lens 48 is preferably positioned so that the intermediate annular beam 38 is formed at the entrance of the scanning module 32, which corresponds to the plane conjugate with the back focal plane of the objective lens 50. One skilled in the art will understand that this may be accomplished by positioning the Fourier-transform lens so that its front focal plane coincides with the entrance of the scanning module 32, as illustrated in FIG. 5A, where it is seen that the intermediate annular beam 38 produced by the Fourier-transform lens 48 has a radius $R=f_\alpha \tan\beta$ at the entrance of the scanning module 32, where $f_\alpha$ is the focal length of the Fourier-transform lens 48.

Imaging Module

Still referring to FIG. 5A, the laser scanning imaging system 20 further includes an imaging module 30.

The imaging module 30 first includes an objective lens 50. It is to be understood that the term "objective lens" generally refers to any lens or system of lenses that forms an image of an object. The term is meant to encompass both refractive and reflective objective lenses.

The objective lens 50 is formed and disposed so as to receive the intermediate annular beam 38 and convert the same into an excitation non-diffracting beam 40 for projection onto the volume 22 of the sample 24.

In the embodiment illustrated in FIG. 5A, the objective lens 50 is preferably formed and disposed so as to generate a Bessel-Gauss beam as the excitation non-diffracting beam 40. Therefore, in some embodiments, both the intermediate non-diffracting beam 36 and the excitation non-diffracting beam 40 are Bessel-Gauss beams. One of ordinary skill in the art will understand that, similarly to the Fourier-transform lens 48, the objective lens 50 in the embodiment of FIG. 5A performs an inverse Fourier transform on the intermediate annular beam 38 by converting it back into a non-diffracting Bessel-Gauss beam, namely the excitation non-diffracting beam 40.

The intensity distribution of the excitation non-diffracting beam 40 at the volume 22 of the sample 24 can therefore have the same profile as the intermediate non-diffracting beam 36 given by Equation (2). However, because of the magnification experienced by the intermediate annular beam 38, the excitation non-diffracting beam 40 is scaled down compared to the intermediate non-diffracting beam 36. As a result, Equation (2) can be used to described the intensity profile of the excitation non-diffracting beam 40 provided that the beam width $w_0$ and deflection angle $\beta$ are replaced by a scaled down beam width $w_f$ and a scaled down deflection angle $\beta_f$, respectively. The scaled down beam width $w_f$ and deflection angle $\beta_f$ may be expressed as follows:

$$w_f = \frac{w_0 F}{m f_\alpha}, \tag{6}$$

$$\beta_f = \tan^{-1}\left(\frac{m f_\alpha}{F} \tan\beta\right). \tag{7}$$

where F is the effective focal length of the objective lens 50 and m is the magnification experienced by the intermediate annular beam 38 as it goes through the scanning module 32 and is relayed to the objective lens 50. Referring to FIG. 4, a schematic ray-trace representation of the propagation and transformation of the input laser beam 28 as it travels through the laser scanning imaging system 20 is depicted. FIG. 4 illustrates how the provision of a beam shaping module 34 including an axicon 44 and a Fourier-transform lens 48 between the laser module 26 and the objective lens 50 allows for the generation of an excitation non-diffracting beam 40 (e.g. a Bessel-Gauss beam) having an extended depth of field through successive transformations of an input laser beam 28 (e.g. a Gaussian beam).

Figure 5B:
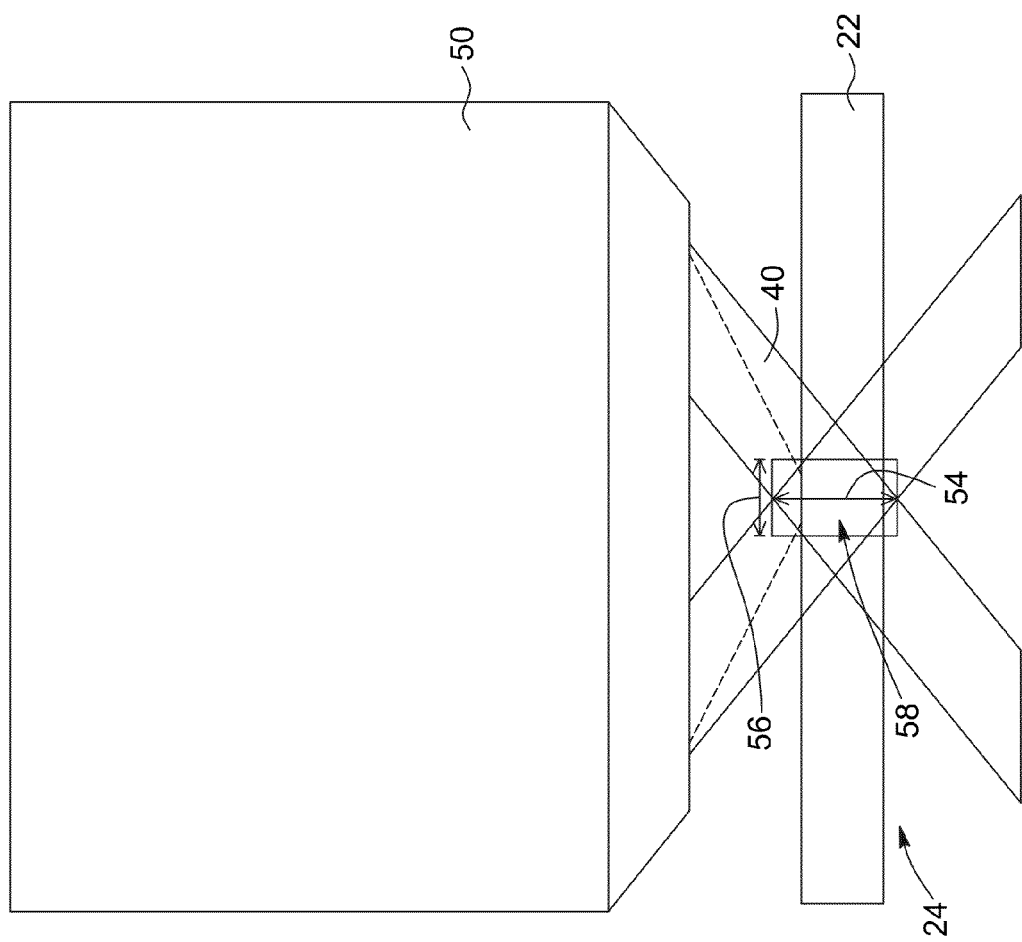
FIG. 5B is an enlarged view of a portion of FIG. 5A depicting the extended depth of field achieved by the laser scanning imaging system.

Referring now to FIG. 5B, which is an enlarged view of a portion of the embodiment of FIG. 5A, the excitation non-diffracting beam 40 has a depth of field 54 (denoted by the symbol $L_f$), and a transverse resolution 56 (denoted by the symbol $\rho_f$), that together define an excitation region 58 within the volume 22 of the sample 24. By looking at Equations (3) and (4), the following analogous expressions can be derived for the transverse resolution 56 and the depth of field 54 of the excitation non-diffracting beam 40:

$$\rho_f = \frac{2.4048\lambda}{2\pi\beta_f}, \tag{8}$$

$$L_f = C\left(\frac{w_f}{\beta_f}\right). \tag{9}$$

It will be understood by one of ordinary skill in the art that Equations (6) to (9) are obtained using small angle approximations, so that they are strictly valid only for objective lens with low numerical apertures. For objectives with high numerical apertures, the vector nature of the electromagnetic fields should be considered when calculating the intensity distribution [Botcherby et al., "Scanning two photon fluorescence microscopy with extended depth of field", *Optics Communications* vol. 268, p. 253-260 (2006)].

Upon examining Equations (6) to (9), one of ordinary skill in the art can see that the transverse resolution 56 and the depth of field 54 of the excitation non-diffracting beam 40 depend on and can be controlled by adjusting any one the following parameters: (i) the wavelength $\lambda$ and width $w_0$ of the input laser beam 28; (ii) the parameters $\alpha$ and $n_2$ of the axicon 44; (iii), the focal length $f_\alpha$ of the Fourier-transform lens 48; (iv) the magnification m imposed by the scanning module 32; and (v) the effective focal length F of the objective lens 50.

One of ordinary skill in the art will also recognize the potential benefits of using, within the beam shaping module 34, a Fourier-transform lens 48 with an adjustable focal length. As mentioned above, this is because the depth of field 54 and the transverse resolution 56 of the excitation non-diffracting beam 40 may be adjusted without having to substitute, realign, calibrate or otherwise modify any of the optical elements that are commonly found in conventional laser scanning imaging systems. Additionally or alternatively, it may be advantageous, as mentioned above, that the laser scanning imaging system 20 be provided with a beam-width control module 46 for controlling the diameter, width or magnification of the input laser beam 28 before it reaches the beam shaping module 34, as controlling these size parameters of the input laser beam 28 allows for a control over the depth of field 54 of the excitation non-diffracting beam 40 while keeping constant its transverse resolution 56.

For example, as the peak intensity of the excitation non-diffracting beam 40 scales as the inverse of the depth of field 54, the excitation non-diffracting beam 40 typically has its power spread over some extended distance along the propagation axis and a more intense input laser beam 28 is generally needed to excite a fluorescence signal from the excitation region 58. This underlines the advantage of being able to adjust the depth of field 54 of the excitation non-diffracting beam 40 to the thickness of the volume 22 of the sample 24.

Embodiments of the present invention may therefore allow for the possibility of controlling the depth of field 54 of the excitation non-diffracting beam 40 to provide an excitation region 58 whose thickness corresponds or is adjusted to that of the sample 24. Such adjusting capabilities can prove to be particularly valuable in applications where extended depth of field is desired or required. In particular, this could enhance the flexibility of the extended-depth-of-field laser imaging system according to embodiments of the invention and optimize the power yield at the sample.

Referring back to FIG. 5A, the imaging module 30 also includes a detecting assembly 60 for collecting electromagnetic radiation 62 from the excitation region 58 and for obtaining therefrom one of a plurality of pixels of the extended-depth-of-field image of the volume 22 of the sample 24.

As used herein, the term "electromagnetic radiation" when referring to radiation originating from the excitation region as a result of the probing of the same by the excitation non-diffracting beam is understood to encompass not only fluorescence radiation emitted within the excitation region, but also electromagnetic radiation reflected and/or scattered and/or transmitted by the sample or any other type of radiation which can result from the interaction of the excitation non-diffracting beam and the volume of the sample.

In the exemplary embodiment of FIG. 5A, the electromagnetic radiation 62 originating from the excitation region 58 is preferably re-collected by the objective lens 50 and toward and onto the detecting assembly 60. For this purpose, the imaging module 30 may include a light separation element 52 arranged in the path of the intermediate annular beam 38 before the same reaches the objective lens 50. The light separation element 52 directs the intermediate annular beam 38 from the scanning module 32 to the objective lens 50, and directs the electromagnetic radiation 62 originating from the volume 22 of the sample 24 on a path to the detecting assembly 60. The light separation element 52 may be embodied by a dichroic mirror or another device or combinations of devices able to separate the excitation illumination from the light emanating from the volume 22 of the sample 24 as a result of this excitation.

In some embodiment, the light separation element 52 may include an additional barrier filter (not shown) to receive the electromagnetic radiation 62 re-collected by the objective lens 50 and separate the fluorescent light from the reflected and scattered light at the source wavelength and direct the same onto the detecting assembly 60. Furthermore, while the embodiment of FIG. 5A depicts the re-collection of electromagnetic radiation 62 emitted in a direction opposite to the input beam (i.e. toward the objective lens 50), in other embodiments the electromagnetic radiation 62 originating from the excitation region 58 can also be done in other directions such as, for example, along the transmission path or the de-scanned path.

In FIG. 5A, the detecting assembly 60 includes a detector 68, which is embodied by a photomultiplier tube. However, other types of detectors could be used without departing from the scope of the present invention such as, for example, avalanche photodiodes, charge-coupled-device (CCD) cameras, complementary metal-oxide-semiconductor (CMOS) cameras or electron multiplying CCD (EMCCD) cameras.

The fluorescence emission incident on the detector 68 may be transformed into an electrical signal and recorded by a processor 70 provided in the detecting assembly 60. The processor may be a computer, a micro-controller, or any appropriate type of processing unit. The processor 70 is preferably used to generate, from the fluorescence emission produced by portion of the volume 22 of the sample 24 within the excitation region 58 defined by the excitation non-diffracting beam 40, one pixel of the extended-depth-of-field image of the volume 22 of the sample 24.

Two-Dimensional Scanning Module

Still referring to FIG. 5A, the laser scanning imaging system 20 further includes a two-dimensional scanning module 32 for scanning the excitation non-diffracting beam 40 over the sample 24 so as to build the extended-depth-of-field image of the volume 22 of the sample 24 from the plurality of pixels thereof.

As mentioned above, in some embodiments, the entrance of the scanning module 32 may coincide with the front focal plane of the Fourier-transform lens 48 (i.e. at a distance $f_\alpha$ after the Fourier-transform lens 48), while the exit of the scanning module 32 may coincide with the back focal plane of the objective lens 50 of the imaging module 30. It will be understood that in such embodiments, the front focal plane of the Fourier-transform 48 corresponds to the plane conjugate with the back focal plane of the objective lens 50. This allows for the intermediate annular beam 38 generated by the Fourier-transform lens 46 to be imaged to the back focal plane of the objective lens 50 and be converted by the objective lens into the excitation non-diffracting beam 40.

As one of ordinary skill in the art will understand, laser scanning microscopy commonly involves a scanning of the laser beam over the sample in order to build, on a pixel-by-pixel basis, an image of the sample. Each pixel represents the observation of one volume element of the sample. In conventional laser scanning microscopy, the scan performed to obtain a complete image of a sample usually involves a three-dimensional scan. Such a three-dimensional scan usually consists of a stack of two-dimensional scans taken at different depths across the thickness of the sample. In contrast, embodiments of the present invention allow for a volumetric image of relatively thick samples or volumes of a sample to be built from a single two-dimensional scan thereof. This is achievable, inter alia, by the conversion of an input laser into an excitation non-diffracting beam having an extended depth of field.

Still referring to FIG. 5A, the two-dimensional scanning module 32 may include a first and a second deflecting elements 64a, 64b disposed in a path of the intermediate annular beam 38 for changing an angle of incidence of the intermediate annular beam 38 on the objective lens 50 along two orthogonal directions x and y, so as to cause the excitation non-diffracting beam 40 to scan the volume 22 of the sample 20 in two dimensions. In some embodiments, the scanning module may further include a first pair of relay lenses 66a, 66b disposed between the first and second deflecting elements 64a, 64b and a second pair of relay lenses 66c, 66d disposed between the second deflecting element 64b and the objective lens 50.

As will understood by one of ordinary skill in the art, rotating the deflecting elements 64a, 64b about respective pivot axes enables tilting the intermediate annular beam 38 along the back focal plane of the objective lens 50 in the x and y directions, respectively which allows for a two-dimensional scan of the excitation non-diffracting beam 40 over the volume 22 of the sample 24 to be performed. It will be understood that the scanning module 32 may scan the volume 22 of the sample 24 whose extended-depth-of-field image is to be obtained according to various scanning patterns or configurations. These may include, without being limited to, a line scan, a sawtooth scan, a raster scan, a bidirectional raster scan, a Lissajous scan, a random access scan, and the like.

In the illustrated embodiment, the deflecting elements 64a, 64b are embodied by scanning mirrors such as, for example, galvanometric mirrors, while the first and second pairs of relay lenses 66a, 66b and 66c, 66d are embodied by pairs of achromatic doublets of equal focal length. Of course, other optical components may be used in place of the deflecting element and/or relays lenses without departing from the scope of the invention. For example, in other embodiments, the two-dimensional scanning module 32 may include a resonance scanner, a piezoelectrical scanner, a rotary polygon scanner, an ultrasonic vibrator deflector, a prism module (e.g. a pair of wedge prisms such as Risley prisms), an electro-optic deflector, and the like. Furthermore, in these or other embodiments, the scanning module 32 need not include the first pair of relay lenses 66a, 66b between the pair of deflecting element 64a, 64b.

Laser Scanning Imaging Method

Figure 10:
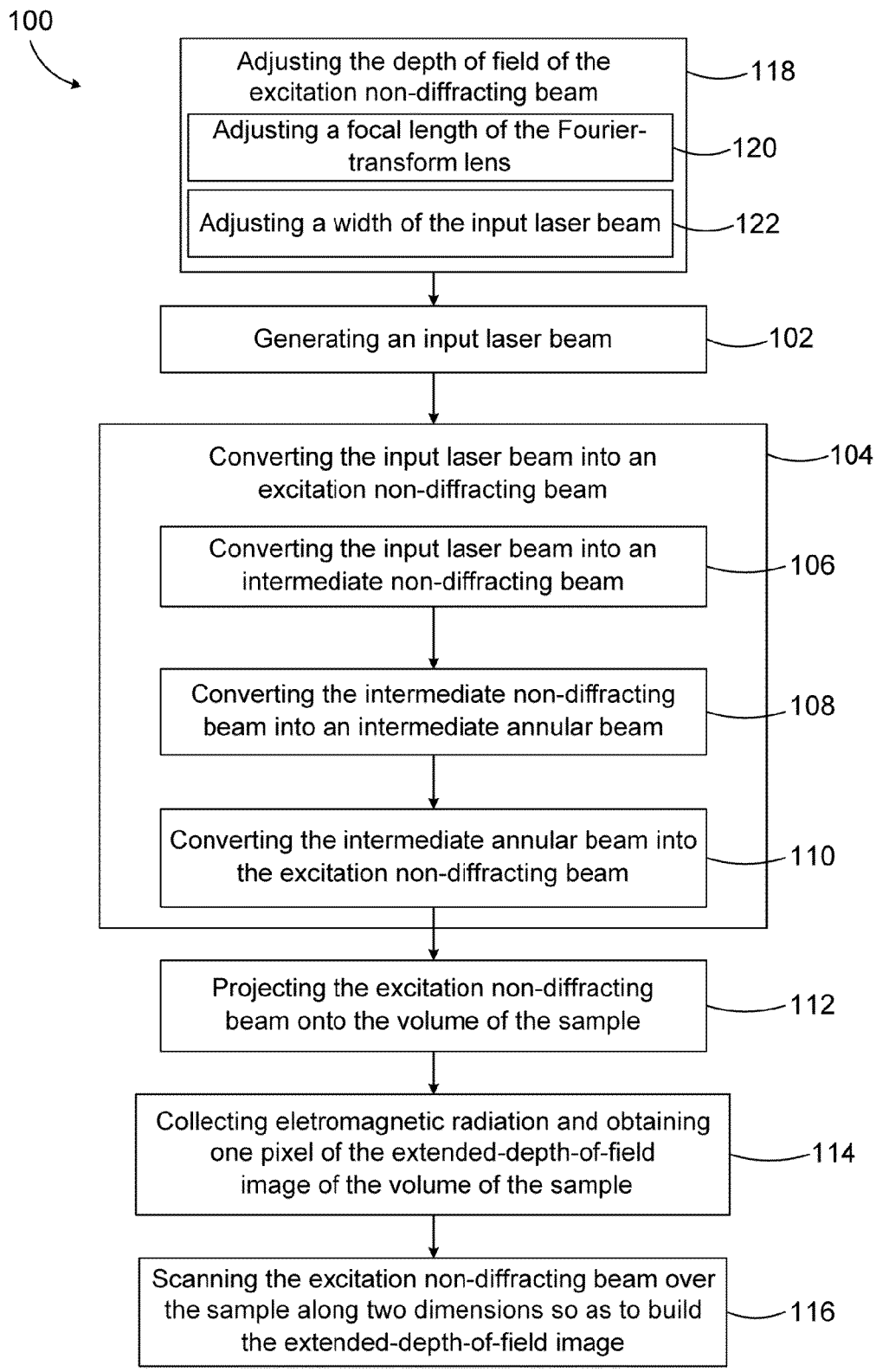
FIG. 10 is a flow chart of a method for obtaining an extended-depth-of-field image of a volume of a sample using laser scanning imaging, in accordance with an embodiment of the invention.

In accordance with another aspect of the invention, there is provided a method for obtaining an extended-depth-of-field image of a volume of a sample using laser scanning imaging. FIG. 10 shows a flow chart of an embodiment of the method 100, which could, by way of example, be performed with a laser scanning imaging system 20 such as that illustrated in FIGS. 5A, 5B and 6.

The method 100 first includes a step 102 of generating an input laser beam. The input laser beam may have different optical characteristics (e.g. wavelength, frequency, intensity, polarization, and size) depending on the intended application of the method 100. In particular, the input laser beam 28 may be generated with a frequency lying in any appropriate portion region of the electromagnetic spectrum, including the visible, infrared and ultraviolet frequency ranges. Preferably, the input laser beam is a pulsed laser beam, but may also be a continuous-wave beam. Also preferably, the step 102 of generating an input laser involves generating a Gaussian laser beam whose transverse electrical field and intensity distribution are well approximated by Gaussian functions.

The method also includes a step 104 of converting the input laser beam into an excitation non-diffracting beam. In embodiments of the method 100, the step 104 of converting is generally performed in three stages, which are described below.

First, the converting step 104 includes a substep 106 of converting the input laser beam into an intermediate non-diffracting beam by causing the input laser beam to pass through an axicon. In embodiments of the method 100 where the input laser is a Gaussian beam, the axicon is formed and disposed to convert this Gaussian beam into a Bessel-Gauss beam, such as that shown in FIG. 3 (PRIOR ART). As mentioned above, a Bessel-Gauss beam represents a close approximation to an ideal Bessel beam, which retains the non-diffractive nature of its central peak.

The converting step 104 also includes a substep 108 of converting the intermediate non-diffracting beam into an intermediate annular beam by causing the intermediate non-diffracting beam to pass through a Fourier-transform lens. As mentioned above, the Fourier lens can be used to perform a two-dimensional Fourier transform on the intermediate non-diffracting beam in order to generate the intermediate annular beam. As was also mentioned, Bessel beams and annular beams are closely related through their Fourier transform. Therefore, in embodiments of the method 100 where the intermediate non-diffracting beam is a Bessel-Gauss beam, the Fourier-transform lens 48 may be used to produce the intermediate annular beam 38.

The converting step 104 further includes a substep 110 of converting the intermediate annular beam into the excitation non-diffracting beam by causing the intermediate annular beam to pass through an objective lens. As described above this may be accomplished, for example, by imaging the intermediate annular beam into the back focal plane of the objective lens, that is, by ensuring that the front focal plane of the Fourier-transform is optically conjugate with the back focal plane of the objective lens.

Preferably, the substep 110 of converting the intermediate annular beam into the excitation non-diffracting beam involves forming and disposing the objective lens so as to generate a Bessel-Gauss beam as the excitation non-diffracting beam. Therefore, in some embodiments of the methods 100, both the intermediate non-diffracting beam and the excitation non-diffracting beam are Bessel-Gauss beams, both with an extended depth of field.

One of ordinary skill in the art will understand that, while in the step 108 of converting the intermediate non-diffracting beam into an intermediate annular beam involved performing the Fourier transform of the intermediate non-diffracting beam, the step of 110 of converting the intermediate annular beam into the excitation non-diffracting beam generally involves performing an inverse Fourier transform on the intermediate annular beam by converting it back into an excitation non-diffracting beam having a Bessel-Gauss profile.

The method 100 further includes a step 112 of projecting the excitation non-diffracting beam onto volume of the sample. As illustrated in FIG. 5B, in connection with the laser scanning imaging system 20 according to an embodiment of the invention, the excitation non-diffracting beam has a depth of field and a transverse resolution that together define an excitation region within the volume of the sample.

The method 100 also includes a step 114 of collecting electromagnetic radiation from the excitation region and obtaining therefrom one of a plurality of pixels of the extended-depth-of-field image of the volume of the sample.

The method 100 further includes a step 116 scanning the excitation non-diffracting beam over the sample along two-dimensions so as to build the extended-depth-of-field image of the volume of the sample from the plurality of pixels thereof. It will be understood that embodiments of the method may allow for the acquisition of a three-dimensional, extended-depth-of-field image of a relatively thick sample by performing only a two-dimensional scan thereover.

Still referring to FIG. 10, in some embodiments, the method 100 may include an optional step 118 of adjusting the depth of field of the excitation non-diffracting beam to substantially match a thickness of the volume of the sample. This may be performed by adjusting 120 a focal length of the Fourier-transform lens. Additionally, or alternatively, this may be performed by adjusting 122 a width of the input laser beam.

As mentioned above, adjusting the depth of field of the excitation non-diffracting beam as a function of the thickness of the sample can provide various benefits. Indeed, as also mentioned above, because the peak intensity of the excitation non-diffracting beam scales as the inverse of the depth of field, the excitation non-diffracting beam typically has its power spread over some extended distance along the propagation axis and a more intense input laser beam is generally needed to excite a fluorescence signal from the excitation region. Therefore, being able to adjust the depth of field of the excitation non-diffracting beam, and thus the thickness of the excitation region, to the thickness of the volume of the sample can prove valuable. Such adjusting capabilities can prove to be particularly beneficial in applications where extended depth of field is desired or required.

In accordance with another aspect of the invention, there is provided a method for extending a depth of field of a laser scanning imaging system. For example, the laser scanning imaging system may be built similarly to standard laser scanning microscopy systems such as that shown in FIG. 1 (PRIOR ART), in that it generally includes a laser module configured to generate an input laser beam, an imaging module including an objective lens for projecting the input laser beam onto a volume of a sample and a detecting assembly for collecting electromagnetic radiation from the volume of the sample, and a two-dimensional scanning module for scanning the input laser beam over the sample. The laser module, imaging module and scanning modules may be embodied by or be similar to the corresponding modules described above.

The method according to this aspect of the invention includes a step of providing a beam shaping module in a path of the input laser beam between the laser module and the scanning module. The beam shaping module may be embodied by or be similar to the beam shaping module described above.

The beam shaping module first includes an axicon formed and disposed for converting the input laser beam into an intermediate non-diffracting beam. The beam shaping module also includes a Fourier-transform lens formed and disposed for converting the intermediate non-diffracting beam into an intermediate annular beam and for directing, via the scanning module, the intermediate annular beam onto the objective lens for conversion of the same into an excitation non-diffracting beam. The excitation non-diffracting beam has an extended depth of field that defines the depth of field of the laser scanning imaging system.

In some embodiments, the method according to this aspect of the invention may include an optional step of adjusting the depth of field of the excitation non-diffracting beam to substantially match a thickness of the volume of the sample. This may be performed by adjusting a focal length of the Fourier-transform lens or, additionally or alternatively, by adjusting a width of the input laser beam, for example adjusting the magnification of a beam-width control module such as described above. As mentioned above, adjusting the depth of field of the excitation non-diffracting beam as a function of the thickness of the sample can provide various benefits. Therefore, being able to adjust the depth of field of the excitation non-diffracting beam, and thus the thickness of the excitation region, to the thickness of the volume of the sample can prove valuable. Such adjusting capabilities can prove to be particularly beneficial in applications where extended depth of field is desired or required.

Experimental Demonstrations

Experimental demonstrations illustrating the depth-of-field extension capabilities provided by embodiments of the invention will now be described. As one of ordinary skill in the art will understand, the present invention is not limited to these particular experimental demonstrations.

The experimental demonstrations described below were performed with a home-built laser scanning imaging system configured for two-photon microscopy. The home-built system allows for the insertion of a beam shaping module between the laser module and the entrance of the scanning module.

The laser module includes a Ti:sapphire laser [Mira, Coherent (trade name)] with a maximum available power of 900 milliwatts, tuned to a central wavelength of 850 nanometers (nm) in a mode-locked regime. The beam shaping module includes an axicon and a Fourier-transform lens. The axicons are uncoated UVFS conical lenses with angles $\alpha=2.5$ degrees and $\alpha=5$ degrees fabricated by Altechna (trade name) were used. A telescope arrangement is also used to adjust the width of the input laser beam illuminating the axicon. The scanning module is composed of a set of galvanometric mirrors [Cambridge Technologies, 6215HM40B (trade name)] linked by a pair of achromatic doublets of equal focal length and relayed to the microscope objective with a second pair of achromatic doublets with a magnification factor m=1.5.

A dichroic beam splitter [Semrock, 705 nm edge Bright-Line (trade name)] receives the laser beam relayed by the scanning module and directs it toward the sample through the objective lens [Zeiss, Plan-Neofluar 20×, 0.5NA or Zeiss, W N-Achroplan 40×, 0.75 NA (trade names)]. The laser beam transmitted through the objective lens is scanned in two dimensions over the sample by the scanning module. Fluorescence emitted by the sample is re-collected by the objective lens and selectively reflected by the dichroic beam splitter toward a photomultiplier tube [Hamamatsu, R3896 (trade name)]. Data collection and the control of the galvanometric mirrors were performed with the ScanImage software (trade name) [Pologruto et al., "ScanImage: flexible software for operating scanning laser microscopes", *Biomedical Engineering Online*, vol. 2, p. 13 (2003)].

Of course, one of ordinary skill in the art will understand that these optical components and instruments are provided by way of example only, and that the laser scanning imaging system according to an aspect of the invention may be embodied by a number of other components and instruments.

Figure 7:
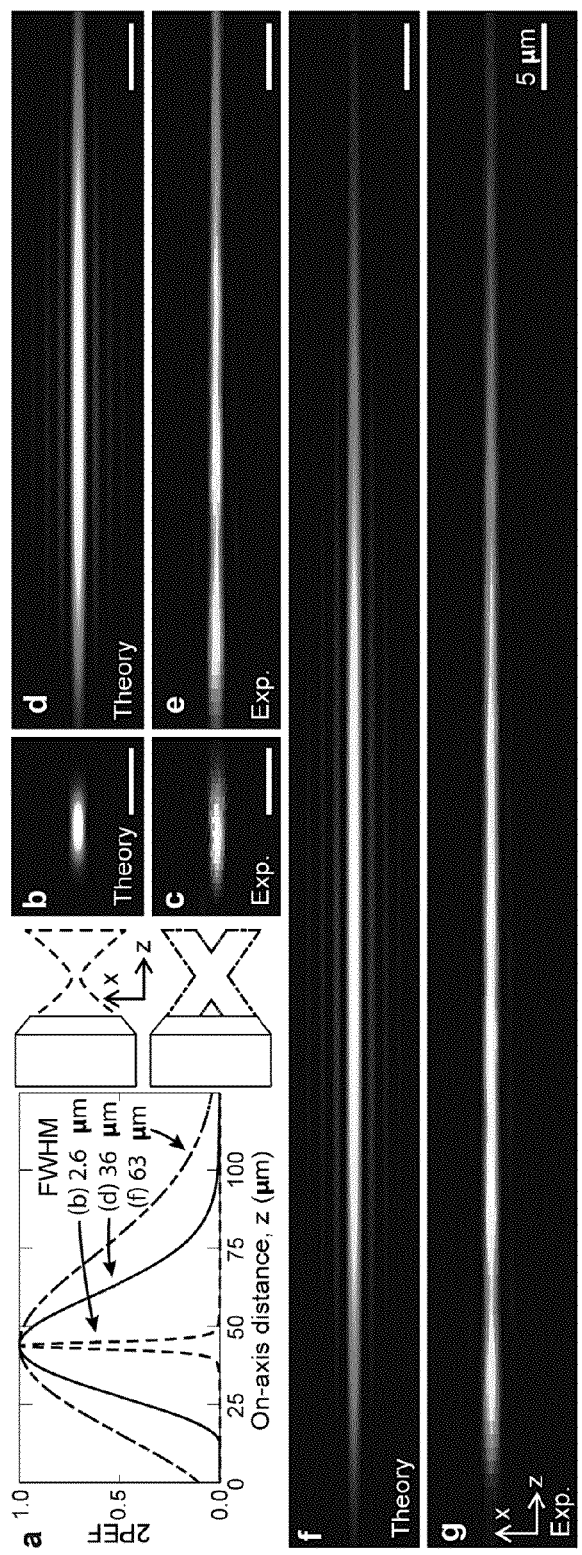
FIG. 7A is a graph of the two-photon excitation fluorescence (2PEF) signal along the propagation axis z for two embodiments of the invention providing an extended depth of field of 36 μm and 63 μm, respectively, and for a standard two-photon laser scanning microscope with a standard depth of field of 2.6 μm.
FIGS. 7B and 7C are respectively the calculated and experimental longitudinal point spread functions in the x-z plane for the standard set-up.
FIGS. 7D and 7E are respectively the calculated and experimental longitudinal point spread functions in the x-z plane for the embodiment with an extended depth of field of 36 μm.
FIGS. 7F and 7G are respectively the calculated and experimental longitudinal point spread functions in the x-z plane for the embodiment with an extended depth of field of 63 µm.

Referring to FIG. 7A, there is shown a graph of the two-photon excitation fluorescence signal along the propagation axis z for two embodiments of the invention providing an extended depth of field of 36 μm and 63 μm, respectively. The fluorescence signal obtained for a standard two-photon laser scanning imaging system with a depth of field of 2.6 μm is also provided for comparison purposes.

FIGS. 7B to 7G illustrate the calculated and experimental longitudinal PSFs in the x-z plane for the standard set-up (FIGS. 7B and 7C), as well as for the embodiments of the invention with an extended depth of field of 36 μm (FIGS. 7D and 7E) and 63 μm (FIGS. 7F and 7G).

Experimental measurements of the PSFs were obtained by mounting fluorescent microspheres (Molecular probes, Fluosphere 505/515, diameter 500 nm) on microscopic slides. Because the microspheres are smaller than the transverse resolution of the laser beam, the collected signal is proportional to the square of the intensity presented in Equation (2). Using $\alpha=5$ degrees, $f_\alpha=60$ millimeters (mm), F=8.25 mm and m=1.5, the two-photon fluorescence distribution in the x-z plane was calculated for two depths of field, namely $L_f=36$ μm with $w_0=0.27$ mm (FIG. 7D) and $L_f=63$ μm with $w_0=0.47$ mm (FIG. 7F). The same parameters were used for the experimental measurements. Each longitudinal PSF was determined from a stack of images acquired by progressively translating the sample by 1 μm in the z direction between each successive acquisition (FIGS. 7E and 7G).

Comparing FIGS. 7B and 7C with each of FIGS. 7D and 7E and FIGS. 7F and 7G, one of ordinary skill in the art will recognize embodiments of the present invention allows for an enhancement of the depth of field in two-photon microscopy. It is to be noted that the standard two-photon fluorescence images shown in FIG. 7C, as well as those described below, were measured simply by removing the beam shaping module, that is, both the axicon and Fourier-transform lens, from the path of the input laser beam. Furthermore, the results shown in FIGS. 7A to 7E illustrate the relationship between the depth of field $L_f$ of a Bessel-Gauss excitation non-diffracting beam and the width $w_0$ of a Gaussian input laser beam, as set out in Equations (6) and (9). More specifically, it can be seen that when the only set-up parameters that changes is the width $w_0$ of the input laser beam incident on the axicon, the depth of field of the excitation non-diffracting beam changes accordingly, while the transverse resolution remains unaffected. However, if any one of the axicon, Fourier-transform lens and objective lens or their parameters were changed, both the depth of field and transverse resolution of the excitation non-diffracting beam would be modified.

Figure 8:
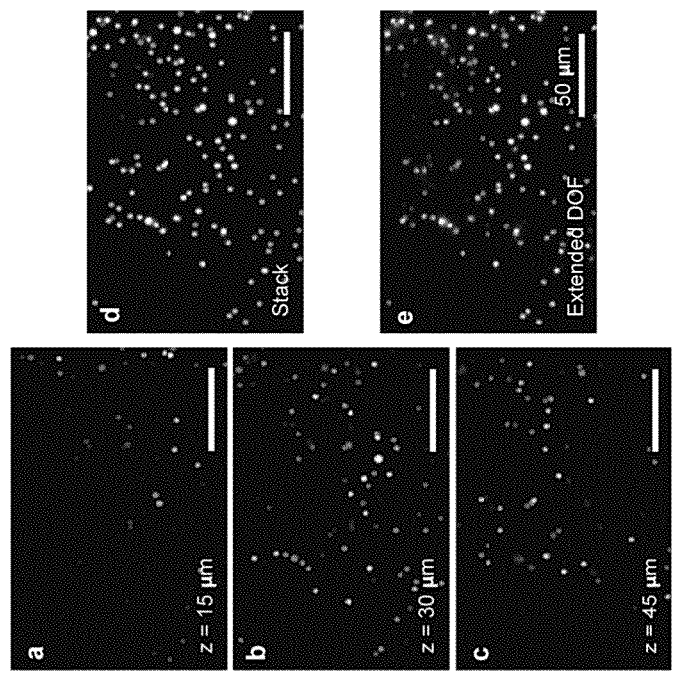
FIGS. 8A to 8C are standard two-photon fluorescence images acquired at various depths by translating a sample of agarose in which fluorescent beads with diameter 3 µm are suspended.
FIG. 8D is a z-averaged stack of thirteen standard two-photon images (including those shown in FIGS. 8A to 8C) spanning a depth of 60 µm.
FIG. 8E is an extended-depth-of-field image of the same sample acquired with the laser scanning imaging system according to an embodiment of the invention.

Referring now to FIG. 8, there is shown experimental results for a block of agarose in which fluorescent beads are suspended (Molecular Probes, diameter of 3 μm). With the standard system, only a few spheres are imaged in each plane, and a stack of thirteen scans had to be acquired to image all the spheres in the volume of interest, spanning a depth of 60 μm (FIGS. 8A to 8D). In FIG. 8E, there is shown an extended-depth-of-field volumetric image of the same sample acquired with a laser scanning imaging system according to an embodiment that includes a conical and a Fourier-transform lens to achieve an extended depth of field of approximately 60 μm. The same parameters as in FIG. 8G were used, namely $w_0=0.47$ mm, $\alpha=5$ degrees, $f_\alpha=60$ mm, F=8.25 mm and m=1.5. With the embodiment of FIG. 8E, it was found that by performing a single two-dimensional scan at the same pixel dwell time as the standard system, all the fluorescent spheres present in the volume were imaged. As the entire volume of interest was scanned in only one frame, this embodiment of the invention provides a thirteen-fold increase in speed when compared to the standard method.

Figure 9:
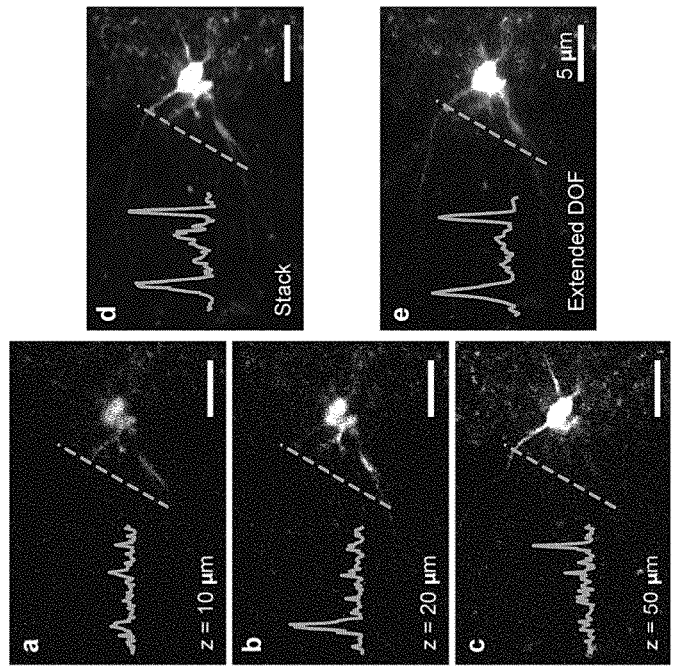
FIGS. 9A to 9C are standard two-photon fluorescence images acquired at various depths by translating a sample of 100-µm thick fixed rat brain slice in which is injected a hippocampal neuron stained with Lucifer Yellow fluorescent dye.
FIG. 9D is a z-averaged stack of twenty-six standard two-photon images (including those shown in FIGS. 9A to 9C) spanning a depth of 60 µm.
FIG. 9E is an extended-depth-of-field image of the same sample acquired with the laser scanning imaging system according to an embodiment of the invention. In each of FIGS. 9A to 9E, the inset curve is the intensity line scan along the dashed line.

Referring to FIGS. 9A to 9E, there is shown how an embodiment of an extended-depth-of-field laser scanning imaging system configured for two-photon microscopy may be used for imaging of biological samples. As an example, a 100-μm thick fixed rat brain slice in which was injected a hippocampal neuron stained with Lucifer Yellow fluorescent dye was studied. By using a standard two-photon set-up, only parts of the dendrites can be observed in a single image, as shown in FIGS. 9A to 9C. In order to image the complete dendritic tree, twenty-six scans had to be acquired, spanning a depth of 50 μm (FIG. 9D). However, with the extended-depth-of-field set-up according with an embodiment of the invention, the same neuron was imaged using the following parameters $w_0=0.7$ mm, $\alpha=2.5$ degrees, $f_\alpha=60$ mm, F=4.125 mm and m=1.5 (FIG. 9E). It is to be noted that although the entire volume of interest could be imaged with only one two-dimensional scan, every line was averaged 5 times to improve the signal-to-noise ratio, therefore leading to about a 5-fold increase in speed.

Upon comparison of FIGS. 9D and 9E, it can be seen that while the z-averaged stack of twenty-six standard two-photon images (FIG. 9D) and the extended-depth-of-field image obtained with an embodiment of the invention (FIG. 9E) depict the same structures, each individual standard-depth-of-field scan only shown parts of the dendrites as they are located at different depths within the sample (FIGS. 9A to 9C). This is illustrated by the intensity line scans inset in each of FIGS. 9A to 9E. The intensity profiles have the same shape for the averaged stack and the extended-depth-of-field images, but the profiles from individual scans with the standard depth of field only show specific parts of the neuron.

Of course, numerous modifications could be made to the embodiments described above without departing from the scope of the present invention.

The invention claimed is:

1. A laser scanning imaging system for obtaining an extended-depth-of-field image of a volume of a sample, the laser scanning imaging system comprising:
   a laser module configured to generate an input laser beam;
   a beam shaping module provided in a path of the input laser beam, the beam shaping module comprising:
      an axicon formed and disposed for converting the input laser beam into an intermediate non-diffracting beam; and
      a Fourier-transform lens formed and disposed for converting the intermediate non-diffracting beam into an intermediate annular beam; and
   an imaging module comprising:
      an objective lens formed and disposed so as to receive the intermediate annular beam and convert the same into an excitation non-diffracting beam for projection onto the volume of the sample, the excitation non-diffracting beam having a depth of field and a transverse resolution together defining a three-dimensional excitation region; and
      a detecting assembly for collecting electromagnetic radiation from the excitation region and for obtaining therefrom one of a plurality of pixels of the extended-depth-of-field image of the volume of the sample; and
   a two-dimensional scanning module for scanning the excitation non-diffracting beam over the sample so as to build the extended-depth-of-field image of the volume of the sample from the plurality of pixels thereof.

2. The laser scanning imaging system according to claim 1, wherein the system is configured for one of two-photon laser scanning microscopy, higher-order multi-photon laser scanning microscopy and confocal laser scanning microscopy.

3. The laser scanning imaging system according to claim 1, further comprising a switching module disposed between the laser module and the beam shaping module, the switching module being operable between a first mode, wherein the switching module directs the input laser beam onto the beam shaping module, and a second mode, wherein the switching module directs the input laser beam onto the imaging module by bypassing the beam shaping module.

4. The laser scanning imaging system according to claim 1, wherein the laser module is configured to generate a Gaussian beam as the input laser beam, and wherein the axicon of the beam shaping module is formed and disposed to generate a Bessel-Gauss beam as the intermediate non-diffracting beam.

5. The laser scanning imaging system according to claim 4, wherein the objective lens of the imaging module is formed and disposed to generate a Bessel-Gauss beam as the excitation non-diffracting beam.

6. The laser scanning imaging system according to claim 1, further comprising a beam-width control module provided in the path of the input laser beam between the laser module and the beam shaping module, adjusting a width of the input laser beam providing an adjustment of the depth of field of the excitation non-diffracting beam.

7. The laser scanning imaging system according to claim 1, wherein the Fourier-transform lens has an adjustable focus, adjusting said focus providing an adjustment of the depth of field of the excitation non-diffracting beam.

8. The laser scanning imaging system according to claim 1, wherein the Fourier-transform lens comprises a front focal plane, the Fourier-transform lens being disposed such that the front focal plane thereof is optically conjugate with a back focal plane of the objective lens.

9. The laser scanning imaging system according to claim 1, wherein the two-dimensional scanning module comprises a first and a second deflecting element disposed in a path of the intermediate annular beam for changing an angle of incidence of the intermediate annular beam on the objective lens along two orthogonal directions.

10. The laser scanning imaging system according to claim 9, wherein the two-dimensional scanning module further comprises a first pair of relay lenses disposed between the first and second deflecting elements and a second pair of relay lenses disposed between the second deflecting element and the objective lens.

11. A method for obtaining an extended-depth-of-field image of a volume of a sample using laser scanning imaging, the method comprising the steps of:
   a) generating an input laser beam;
   b) converting the input laser beam into an excitation non-diffracting beam, comprising the substeps of:
      i) converting the input laser beam into an intermediate non-diffracting beam by causing the input laser beam to pass through an axicon;
      ii) converting the intermediate non-diffracting beam into an intermediate annular beam by causing the intermediate non-diffracting beam to pass through a Fourier-transform lens; and
      iii) converting the intermediate annular beam into the excitation non-diffracting beam by causing the intermediate annular beam to pass through an objective lens; and
   c) projecting the excitation non-diffracting beam onto the volume of the sample, the excitation non-diffracting beam having a depth of field and a transverse resolution together defining a three-dimensional excitation region;

d) collecting electromagnetic radiation from the excitation region and obtaining therefrom one of a plurality of pixels of the extended-depth-of-field image of the volume of the sample; and e) scanning the excitation non-diffracting beam over the sample along two-dimensions so as to build the extended-depth-of-field image of the volume of the sample from the plurality of pixels thereof.

12. The method according to claim 11, wherein, in step a), the input laser beam is a Gaussian beam, and wherein, in substep i) of step b), the intermediate non-diffracting beam is a Bessel-Gauss beam.

13. The method according to claim 12, wherein, in substep iii) of step b), the excitation non-diffracting beam is a Bessel-Gauss beam.

14. The method according to claim 11, further comprising a step of adjusting the depth of field of the excitation non-diffracting beam to substantially match a thickness of the volume of the sample.

15. The method according to claim 14, wherein adjusting the depth of field of the excitation non-diffracting beam comprises adjusting a focal length of the Fourier-transform lens.

16. The method according to claim 14, wherein adjusting the depth of field of the excitation non-diffracting beam comprises adjusting a width of the input laser beam.

17. A method for extending a depth of field of a laser scanning imaging system comprising:
a laser module configured to generate an input laser beam;
an imaging module comprising an objective lens for projecting the input laser beam onto a volume of a sample and a detecting assembly for collecting electromagnetic radiation from the volume of the sample; and
a two-dimensional scanning module for scanning the input laser beam over the sample, the method comprising the step of providing a beam shaping module in a path of the input laser beam between the laser module and the scanning module, the beam shaping module comprising:
an axicon formed and disposed for converting the input laser beam into an intermediate non-diffracting beam; and
a Fourier-transform lens formed and disposed for converting the intermediate non-diffracting beam into an intermediate annular beam and for directing, via the scanning module, the intermediate annular beam onto the objective lens for conversion of the same into an excitation non-diffracting beam, the excitation non-diffracting beam having an extended depth of field that defines the depth of field of the laser scanning imaging system.

18. The method according to claim 17, further comprising adjusting the depth of field of the excitation non-diffracting beam to substantially match a thickness of the volume of the sample.

19. The method according to claim 18, wherein adjusting the depth of field of the excitation non-diffracting beam comprises adjusting a focal length of the Fourier-transform lens.

20. The method according to claim 18, wherein adjusting the depth of field of the excitation non-diffracting beam comprises adjusting a width of the input laser beam.

* * * * *